US011572584B2

(12) United States Patent
Mikkelsen et al.

(10) Patent No.: US 11,572,584 B2
(45) Date of Patent: *Feb. 7, 2023

(54) TARGETED ENRICHMENT OF LONG NUCLEOTIDE SEQUENCES USING MICROFLUIDIC PARTITIONING

(71) Applicant: Samplix ApS, Herlev (DK)

(72) Inventors: Marie Just Mikkelsen, Brønshøj (DK); Thomas Kvist, Roskilde (DK); Esben Bjørn Madsen, Copenhagen (DK)

(73) Assignee: SAMPLIX APS, Herlev (DK)

(*) Notice: Subject to any disclaimer, the term of this patent is extended or adjusted under 35 U.S.C. 154(b) by 344 days.

This patent is subject to a terminal disclaimer.

(21) Appl. No.: 16/921,103

(22) Filed: Jul. 6, 2020

(65) Prior Publication Data
US 2020/0332353 A1    Oct. 22, 2020

Related U.S. Application Data

(63) Continuation of application No. 15/739,541, filed as application No. PCT/EP2016/064719 on Jun. 24, 2016, now Pat. No. 10,738,354.
(Continued)

(30) Foreign Application Priority Data

Jul. 7, 2015    (DK) .............................. PA201570449

(51) Int. Cl.
*C12P 19/34*    (2006.01)
*C12Q 1/6848*    (2018.01)
(Continued)

(52) U.S. Cl.
CPC .......... *C12Q 1/6848* (2013.01); *C12Q 1/686* (2013.01); *C12Q 1/6806* (2013.01)

(58) Field of Classification Search
CPC ..................................................... C12Q 1/686
See application file for complete search history.

(56) References Cited

U.S. PATENT DOCUMENTS

2012/0164633 A1    6/2012    Ibis

FOREIGN PATENT DOCUMENTS

WO    WO 2010/148039    12/2010
WO    WO 2014/096421    6/2014
(Continued)

OTHER PUBLICATIONS

Agresti, J.J., et al., Ultrahigh-throughput screening in drop-based microfluidics for directed evolution. Proc Natl Acad Sci U S A, 2010. 107(9): p. 4004-9.
(Continued)

*Primary Examiner* — Kenneth R Horlick
(74) *Attorney, Agent, or Firm* — Casimir Jones SC; Lisa Mueller

(57) ABSTRACT

The present disclosure relates to methods for enrichment or isolation of a long nucleotide fragment comprising a known nucleotide sequence element, i.e. a sequence encoding a conserved active site or domain, the method being applicable i.a. to high throughput screening for DNA fragments containing a known sequence element. The methods herein comprise the steps of forming an emulsion of multiple liquid droplets from a DNA fragment containing liquid sample, specific detection of droplets containing at least one target DNA molecule, physically selecting droplets containing at least one target DNA molecule, and performing a general amplification of the DNA molecules containing at least one target DNA molecules.

Figure 1:
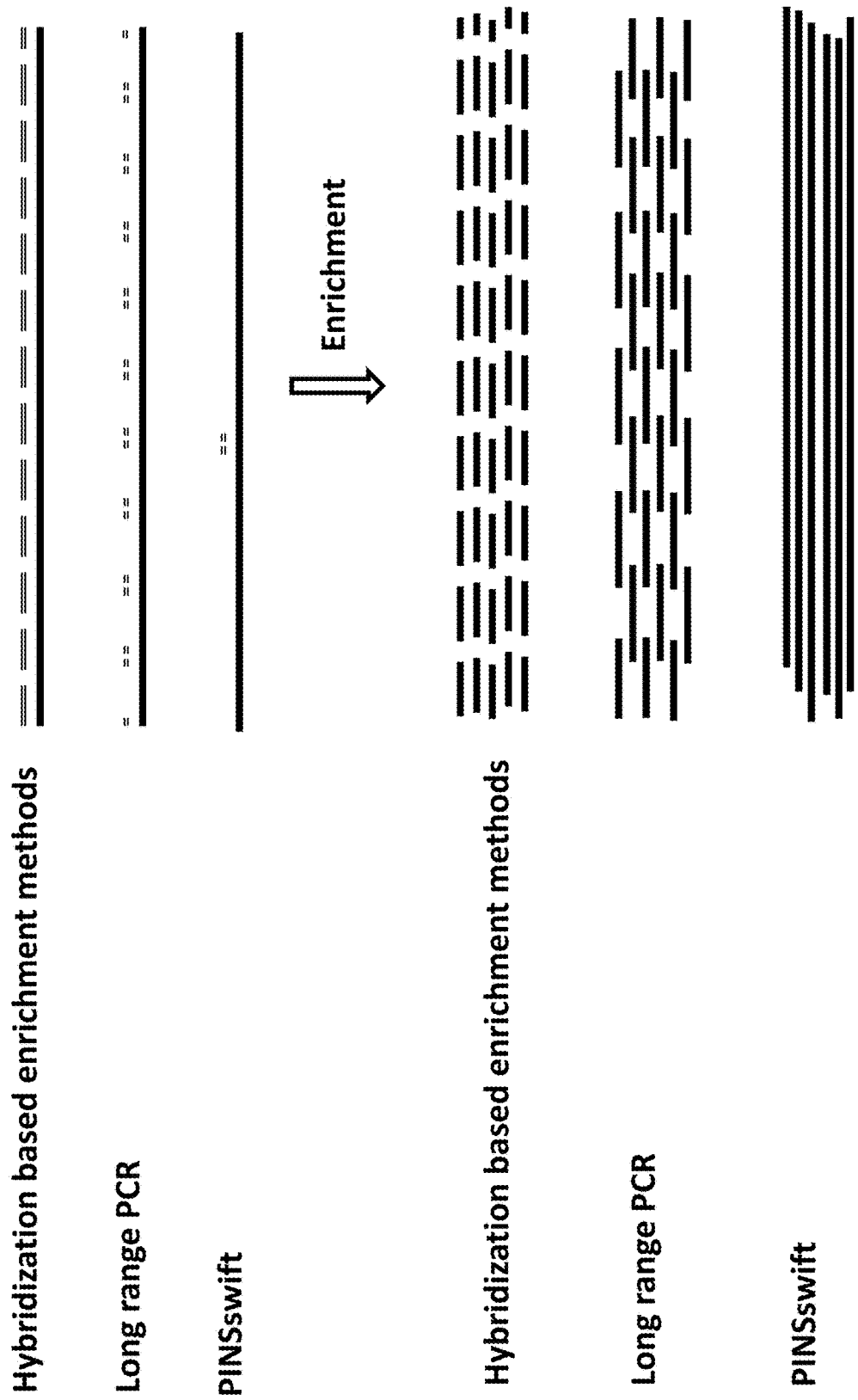

21 Claims, 9 Drawing Sheets
Specification includes a Sequence Listing.

Related U.S. Application Data

(60) Provisional application No. 62/185,111, filed on Jun. 26, 2015.

(51) Int. Cl.
*C12Q 1/6806* (2018.01)
*C12Q 1/686* (2018.01)

(56) References Cited

FOREIGN PATENT DOCUMENTS

| | | |
|---|---|---|
| WO | WO 2014/165762 | 10/2014 |
| WO | WO 2014/172373 | 10/2014 |
| WO | WO 2015/189336 | 12/2015 |
| WO | WO 2015/200717 | 12/2015 |

OTHER PUBLICATIONS

Blainey, P.C. et al: "Digital MDA for enumeration of total nucleic acid contamination", Nucleic Acids Research, 2011, vol. 39, No. 4, e19, pp. 1-9.
Eastburn et al: "Microfluidic droplet enrichment for targeted sequencing" Nucleic Acids Research, 2015, vol. 43, No. 13, e86, pp. 1-8, Published online Apr. 14, 2015.
Hindson, B.J., et al., High-throughput droplet digital PCR system for absolute quantitation of DNA copy number Anal Chem, 2011. 83(22): p. 8604-10.
Kintses, B., et al., Microfluidic droplets: new integrated workflows for biological experiments. Current Opinion in Chemical Biology, 2010. 14(5): p. 548-55.
Kvist, T. et al: "Partition Enrichment of Nucleotide Sequences (PINS)—A Generally Applicable, Sequence Based Method for Enrichment of Complex DNA Samples", PLOS One, 2014, vol. 9, No. 9, e106817, pp. 1-6.
Walter, N.G., Single molecule tools: fluorescence based approaches, part A. Preface. Methods in Enzymology, 2010. 472: p. xxi-xxii.
Liu, Y., S.-Y. Jung, and C.P. Collier, Shear-Driven Redistribution of Surfactant Affects Enzyme Activity in Well-Mixed Femtoliter Droplets. Analytical Chemistry, 2009. 81(12): p. 4922-4928.
Longo, M.C., M.S. Berninger, and J.L. Hartley, Use of uracil DNA glycosylase to control carry-over contamination in polymerase chain reactions. Gene, 1990. 93(1): p. 125-8.
Marcy, Y. et al.: "Nanoliter Reactors Improve Multiple Displacement Amplification of Genomes from Single Cells", PLOS Genetics, 2007, vol. 3, No. 9, e155, pp. 1702-1708.
Mazutis, L., et al: "Droplet-Based Microfluidic Systems for High-Throughput Single DNA Molecule Isothermal Amplification and Analysis", Anatytical Chemistry, 2009,vol. 81, No. 12, pp. 4812-4821.
Pandit, K.R., et al., Assessment of surfactants for efficient droplet PCR in mineral oil using the pendant drop technique. Colloids Surf B Biointerfaces, 2015. 126: p. 489-95.
Prodělalová, J., et al., Isolation of genomic DNA using magnetic cobalt ferrite and silica particles. Journal of Chromatography A, 2004. 1056(1-2): p. 43-48.
Rinke, C., et al., Obtaining genomes from uncultivated environmental microorganisms using FACS-based single-cell genomics. Nat. Protocols, 2014. 9(5): p. 1038-1048.
Sambrook, J. and D.W. Russell, Molecular Cloning a laboratory manual. 2001: Cold Spring Harbor Laboratory Press.
Sharma, S., et al., Droplet-based microfluidics. Methods in Molecular Biology, 2013. 949: p. 207-30.
Tan,Y-C., et al., Monodipersed microfluidic droplet generation by shear focusing microfluidic device. Sensors and Actuators, 2006, B114: 350-356.
Tewhey, R. et al: "Microdoplet-based PCR enrichment for large-scale targeted sequencing", Nature Biotechnology, 2009, vol. 27, No. 11, pp. 1025-1031.

1: Phi29, 1ng target
2: Phi29, no template control
3: Phi29, 1ng target + droplets
4: Phi29, no template control + droplets
5: Non-amplified 1 ng template DNA Templates for qPCR:
1: Phi29, 1ng target (B01-2)
2: Phi29, no template control (B03-4)
3: Phi29, 1ng target + droplets (B05-6)
4: Phi29, no template control + droplets (B07-8)
5: Positive control (B09-10)

TARGETED ENRICHMENT OF LONG NUCLEOTIDE SEQUENCES USING MICROFLUIDIC PARTITIONING

CROSS-REFERENCE TO RELATED APPLICATIONS

This application is a continuation of U.S. patent application Ser. No. 15/739,541, filed on Dec. 22, 2017 (now U.S. Pat. No. 10,738,354), which is a U.S. national stage entry of International Patent Application No. PCT/EP2016/064719, filed on Jun. 24, 2016, which claims priority to Danish Patent Application No. PA 2015 70449, filed on Jul. 7, 2015, and to U.S. Provisional Application No. 62/185,111, filed on Jun. 26, 2015, the entire contents of all of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 25,154 Byte ASCII (Text) file named "2020-07-06_35890-303_SQL_ST25" created on Jul. 6, 2020.

TECHNICAL FIELD

The invention relates to a method for enrichment or isolation of a long nucleotide fragment comprising a known nucleotide sequence element, i.e. a sequence encoding a conserved active site or domain, the method being applicable i.a. to high throughput screening for DNA fragments containing a known sequence element.

BACKGROUND OF THE INVENTION

Sequencing of DNA is a major driver in genetics research. The 'next generation sequencing' technological revolution is gathering momentum as new robust high-throughput sequencing instruments are becoming available. New and improved methods and protocols have been developed to support a diverse range of applications, including analysis of genetic variation. As part of this, methods have been developed that aim to achieve targeted enrichment of genome sub-regions such as targeted cancer panels or complete human exomes. By selective recovery of genomic loci of interest, costs and effort can be reduced significantly compared with whole-genome sequencing.

Current techniques for targeted enrichment fall into three categories; Hybrid capture, selective circularization, and PCR amplification. In hybrid capture techniques, short fragment libraries (typically 100-250 base pairs) are hybridized specifically to complementary DNA fragments so that one can physically capture and isolate the sequences of interest. Selective circularization encompasses methods wherein single-stranded DNA circles including target sequences are formed, creating structures with common DNA elements that are then used for selective amplification of the target sequence. Finally, PCR amplification based enrichment is directed toward the target region by conducting multiple PCR reactions in parallel.

Common for the current enrichment methods is that they require a significant knowledge of the target sequence, a relatively pure sample, a significant amount of target sequence, and that they produce relatively short sequences.

Accordingly there is a need for methods that can be used to analyze complex DNA samples, for example mammalian genomic DNA samples, where the frequency of the target is low (i.e. 1 target copy per genome), and where the analysis does not depend on the individualized analysis of each DNA molecule in the sample, which is both expensive and time consuming.

SUMMARY OF THE INVENTION

The invention, according to a first embodiment, provides an in vitro method for enriching for one of more target DNA molecule from a sample of mixed DNA molecules comprising the steps of:
a) providing a liquid sample of mixed DNA molecules comprising one or more specific target DNA molecule and reagents for specific detection of at least one of said target DNA molecules (401),
b) formation of a multiple of liquid droplets from said liquid sample (403),
c) specific detection of droplets containing at least one of said target DNA molecules (404), wherein each droplet contains less than 0.5, preferably less than 0.25 or even more preferably less than 0.1 of said one of more target DNA molecule on average (404), and
d) physically selecting droplets containing at least one of said target DNA molecules (405),
e) general amplification of the DNA molecules in the coalesced selected droplets, where said DNA molecules are in a total amount of less than 300 fg, wherein general amplification reagents are added to the coalesced droplets to form a general amplification reaction mixture, and wherein from at least $1.2 \times 10^6$ and up to a maximum of $1.2 \times 10^9$ droplets are formed for each 5 µl of the reaction mixture.

The invention, according to a second embodiment, provides an in vitro method for enriching for one of more target DNA molecule from a sample of mixed DNA molecules comprising the steps of:
a) providing a liquid sample of mixed DNA molecules comprising one or more specific target DNA molecule and reagents for specific detection of at least one of said target DNA molecules (401),
b) formation of a multiple of liquid droplets each comprising mixed DNA molecules from said liquid sample (403),
c) specific detection of droplets containing at least one of said target DNA molecules (404), wherein each droplet contains less than 0.5, preferably less than 0.25 or even more preferably less than 0.1 of said one of more target DNA molecule on average (404), and
d) physically selecting droplets containing at least one of said target DNA molecules (405), wherein the frequency of the target DNA molecule compared to its frequency in the sample of mixed DNA molecules in step (a) is increased between 0.01×(total number of droplets containing DNA molecules)×(number of droplets with target DNA)$^{-1}$ and 100×(total number of droplets containing DNA molecules)×(number of droplets with target DNA)$^{-1}$,
e) general amplification of the mixed DNA molecules in the coalesced selected droplets, where the DNA molecules are in a total amount of less than 300 fg, wherein general amplification reagents are added to the coalesced droplets to form a general amplification reaction mixture, and wherein from at least $1.2 \times 10^6$ and up to a maximum of 1.2×10⁹ droplets are formed for each 5 µl of the reaction mixture.

In an alternative to the first or second embodiments, the total amount of DNA (originating from the selected droplets) in step e) is less than 200 fg, or less than 150 fg, or less than 100 fg, or less than 80 fg, or less than 60 fg, or less than 40 fg, or less than 20 fg, or less than 10 fg, or less than 5 fg, or less than 3 fg, or less than 2 fg, or less than 1 fg.

LEGENDS TO THE FIGURES

FIG. 1: Comparison of PINSswift to current methods of specific DNA enrichment. Upper part: The filled black lines represent a DNA target of approximately 30 kb. The dotted lines represent the nucleotide sequence information in respect of the target sequence that is needed in advance in order to perform the enrichment method. The nucleotide sequence information required for PINSswift can be located at any position on the DNA target sequence. Lower part (below the arrow): The black lines represent enriched DNA target molecule showing the difference in the length of the target DNA molecules after the three different types of enrichment.

Figure 2:
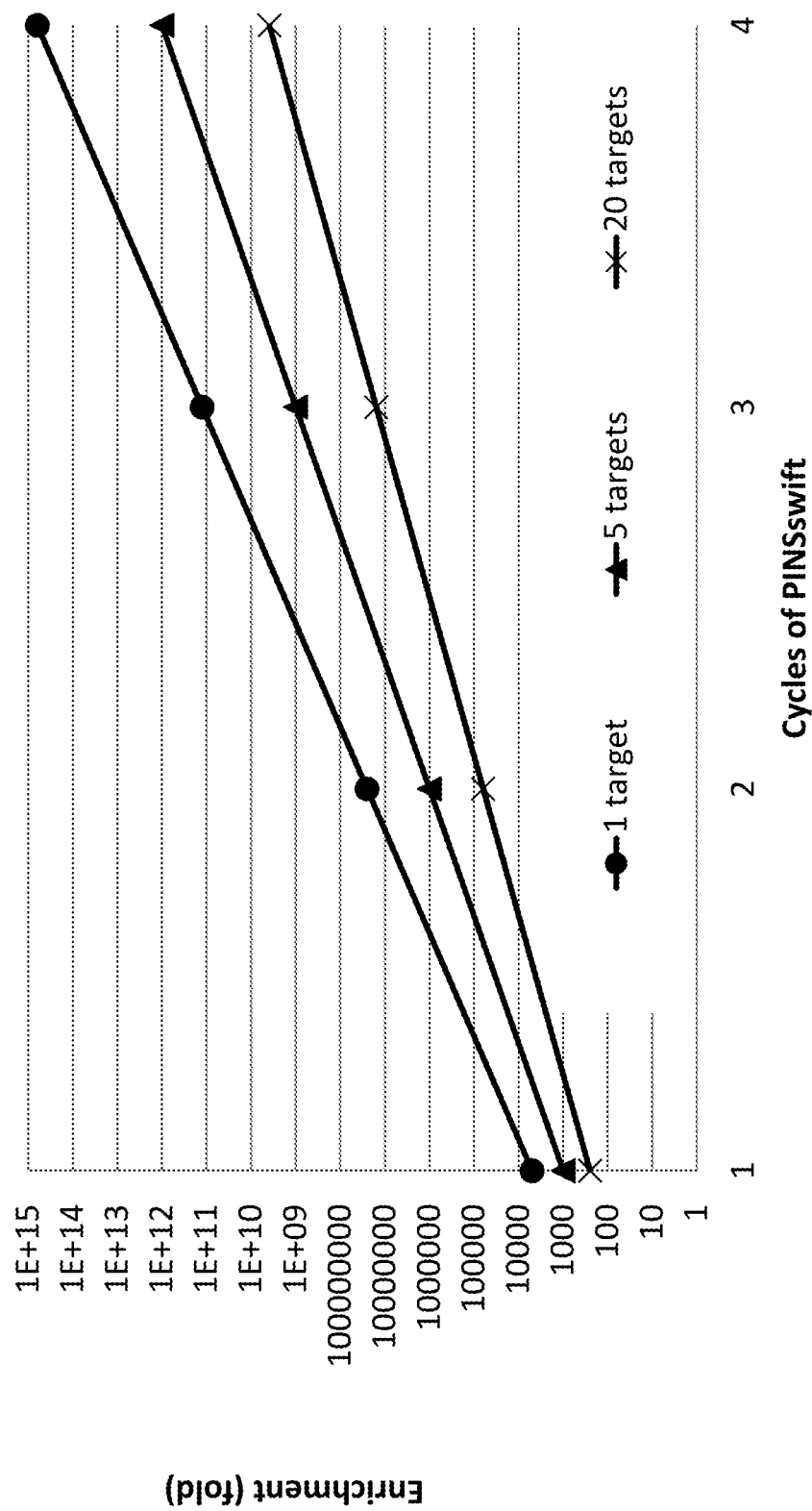

FIG. 2: Enrichment of target DNA molecule (fold enrichment relative to the DNA in the starting sample based on the number of target molecules per ng of total DNA) after 1, 2, 3, and 4 rounds of PINSswift shown for 1, 5 and 20 targets multiplexed in one reaction assuming four positive droplets per target sequence and a total of 20,000 droplets.

Figure 3:
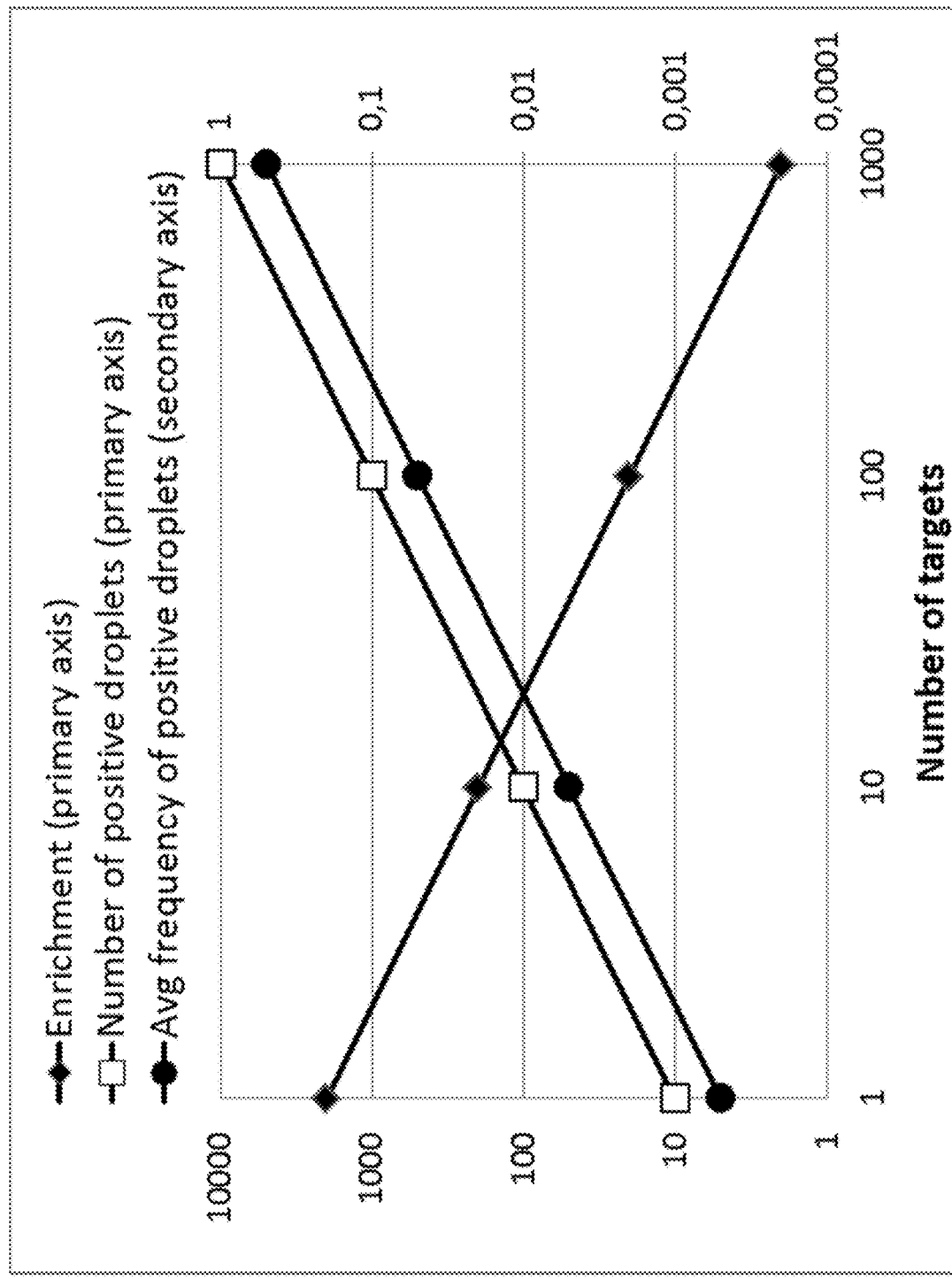

FIG. 3: Correlation between the number of target DNA molecules, the average number of positive droplets and the resulting enrichment of target DNA molecules; exemplified using one round of PINSswift, 20,000 droplets and 10 positive droplets per target.

Figure 4:
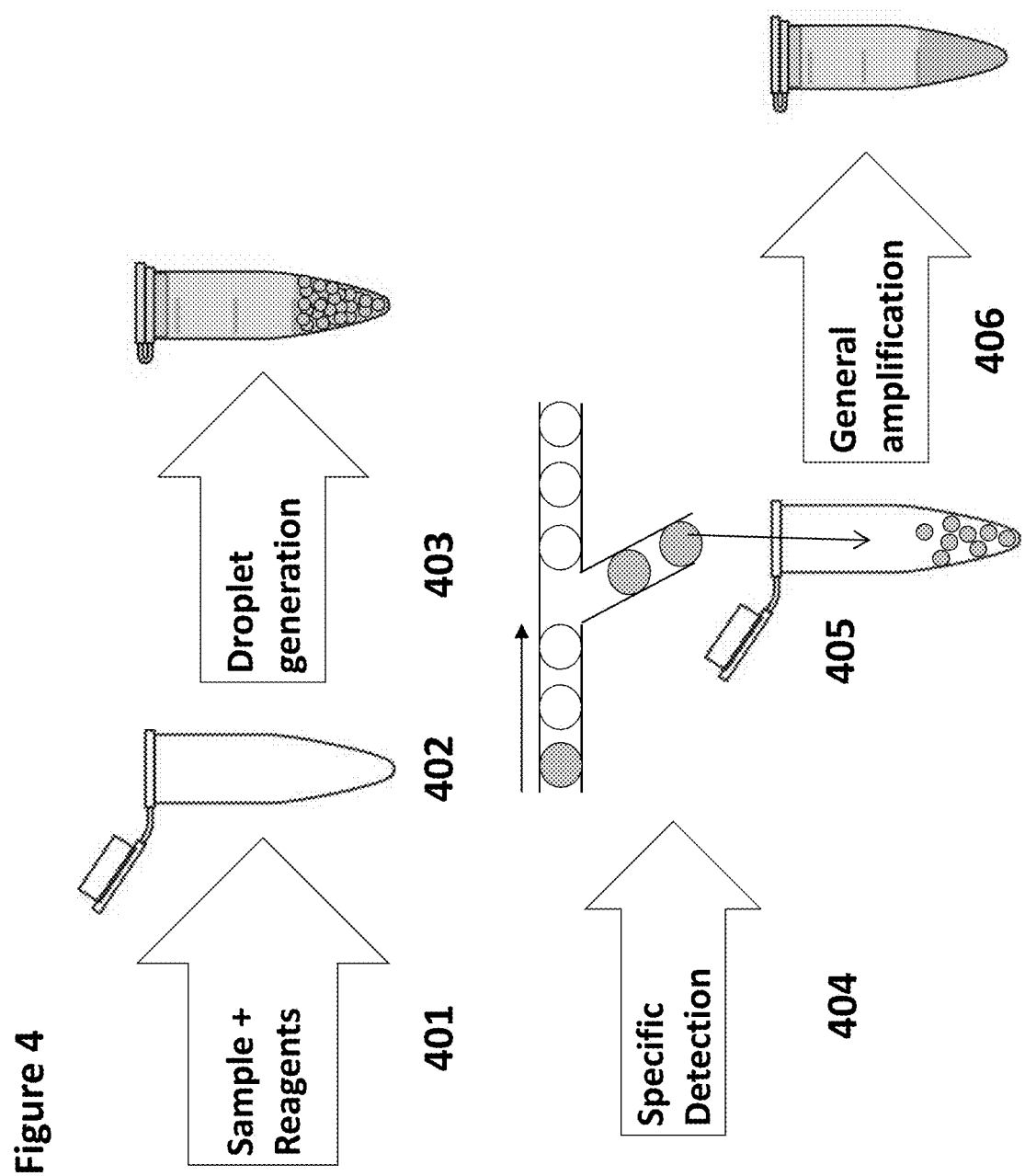

FIG. 4: Outline of a scheme for performing PINSswift
401: DNA sample containing one or more DNA target and reagents for the detection reaction are mixed.
402: Components required for droplet generation are added to the mixture.
403: Droplets containing the DNA and reagents are generated.
404: Reaction steps such as PCR cycling needed for specific detection (optional) are performed.
405: Positive droplets containing target DNA are detected, selected and sorted using an apparatus for physical selection of droplets.
406: General amplification of the DNA from the coalesced positive droplets.

Figure 5:
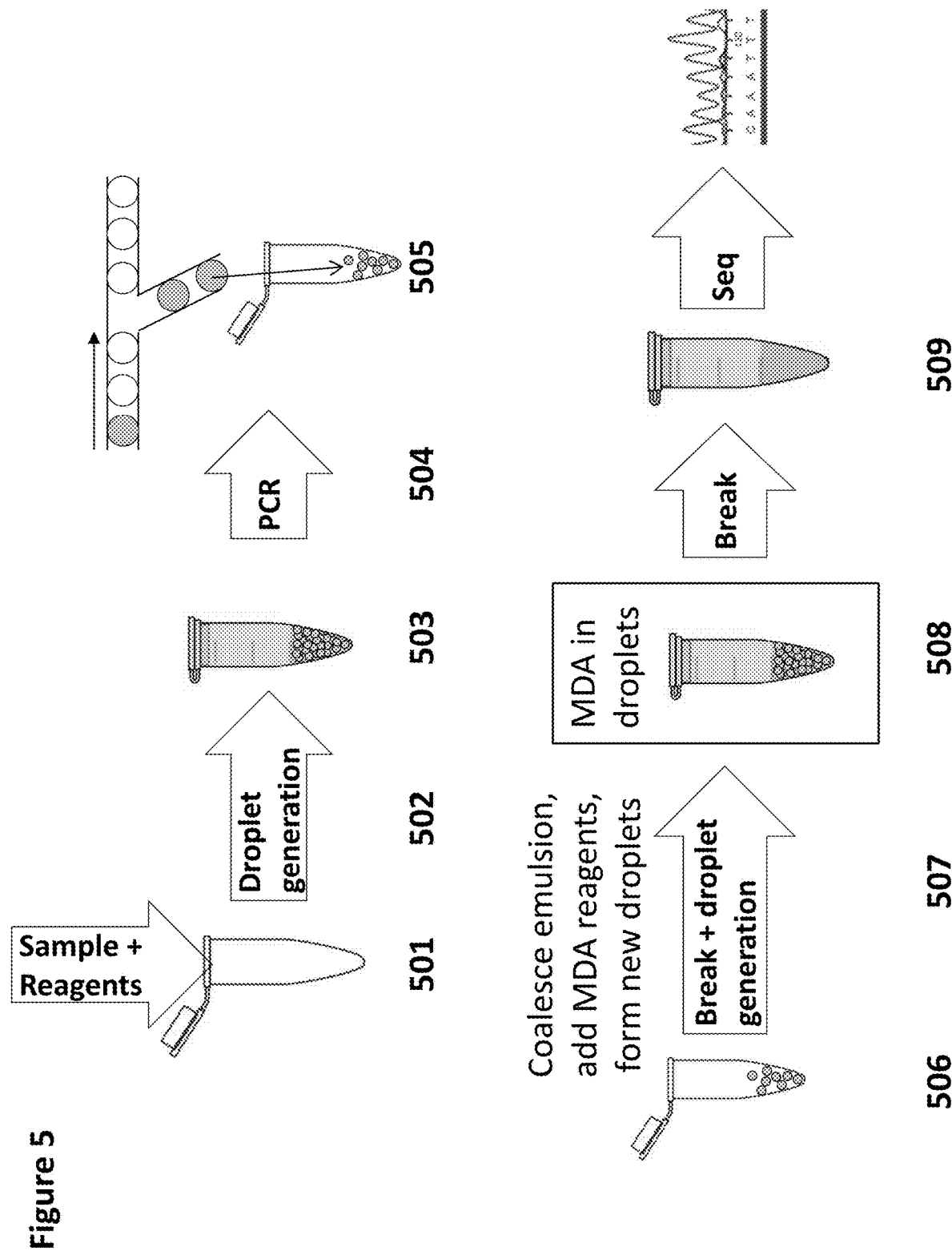

FIG. 5: Outline of a scheme for performing PINSswift as described in Example 1.
501: A DNA sample containing the DNA target and reagents for PCR are mixed.
502: Components required for droplet generation are added to the mixture.
503: Droplets containing the DNA and reagents are generated.
504: PCR amplification of a fragment of the target nucleotide.
505: Positive droplets containing target DNA are detected based on fluorescence generated in PCR, selected and sorted in a microfluidic chip.
506-508: The collected, sorted positive droplets are coalesced, reagents for Phi29 amplification are added to the water phase, new droplets are formed from the water phase by adding oil and mixing, and the mix is incubated at 30° C.
509: The droplets are coalesced and the amplified DNA is purified and sequenced.

Figure 6:
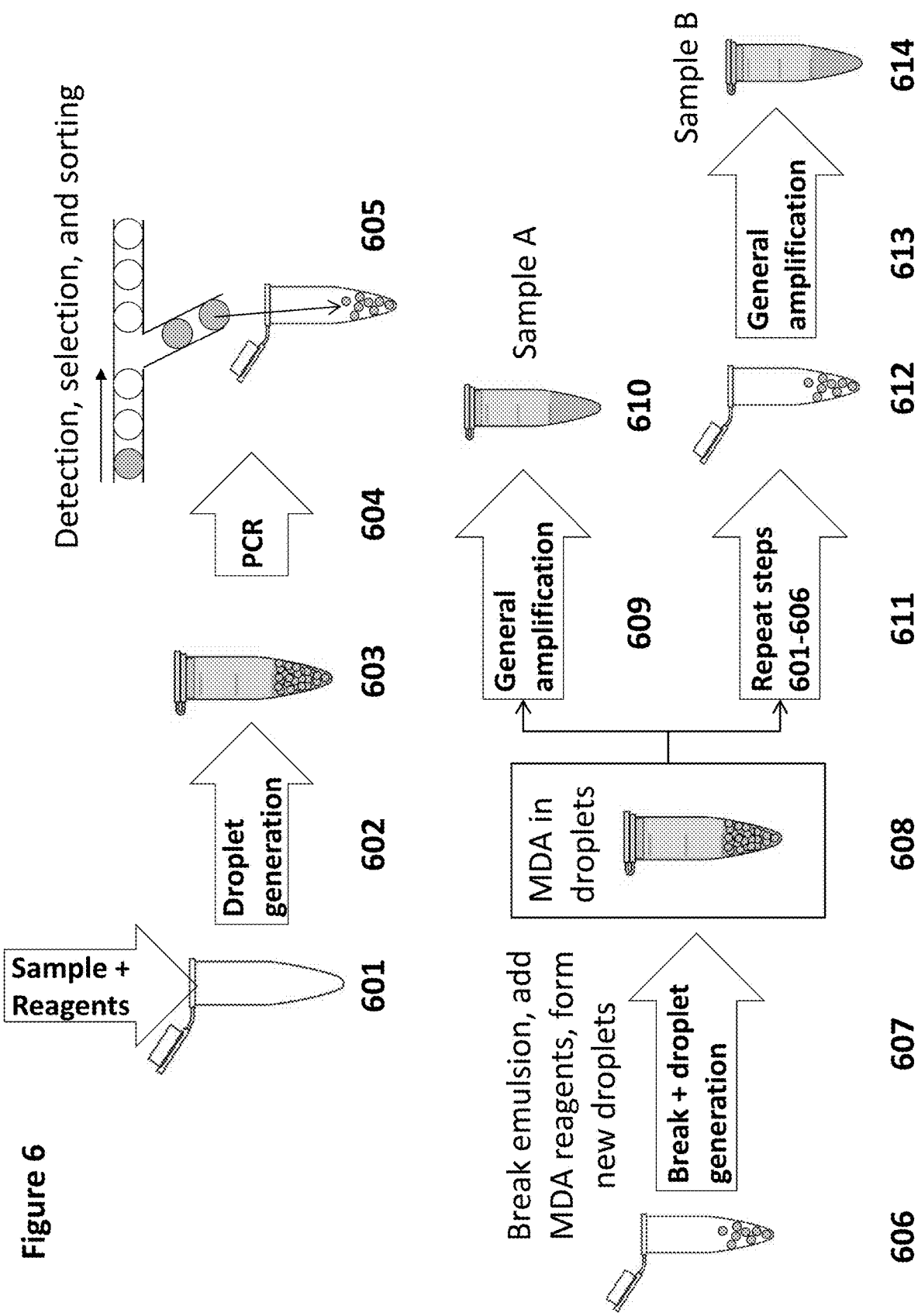

FIG. 6: Outline of a scheme for performing PINSswift as described in example 2.
601: A DNA sample containing the DNA target and reagents for PCR are mixed.
602: Components required for droplet generation are added to the mixture.
603: Droplets containing the DNA sample and reagents are generated.
604: PCR amplification of a portion of the target DNA molecule.
605: Positive droplets containing target DNA molecule are detected based on fluorescence generated in PCR, selected and sorted in a microfluidic chip.
606-608: The collected, sorted positive droplets are coalesced, reagents for Phi29 amplification are added to the water phase, new droplets are generated from the water phase and the droplet emulsion is incubated at 30° C.
609: The sample is further amplified resulting in Sample A (610).
610: A part of Sample 608 is used for a second round of enrichment by dilution and repetition of steps 601 to 606.
611-614: The sorted droplets (612) are coalesced, reagents for Phi29 amplification are added and the DNA fragments are amplified in emulsion to generate Sample B (614).

Figure 7:
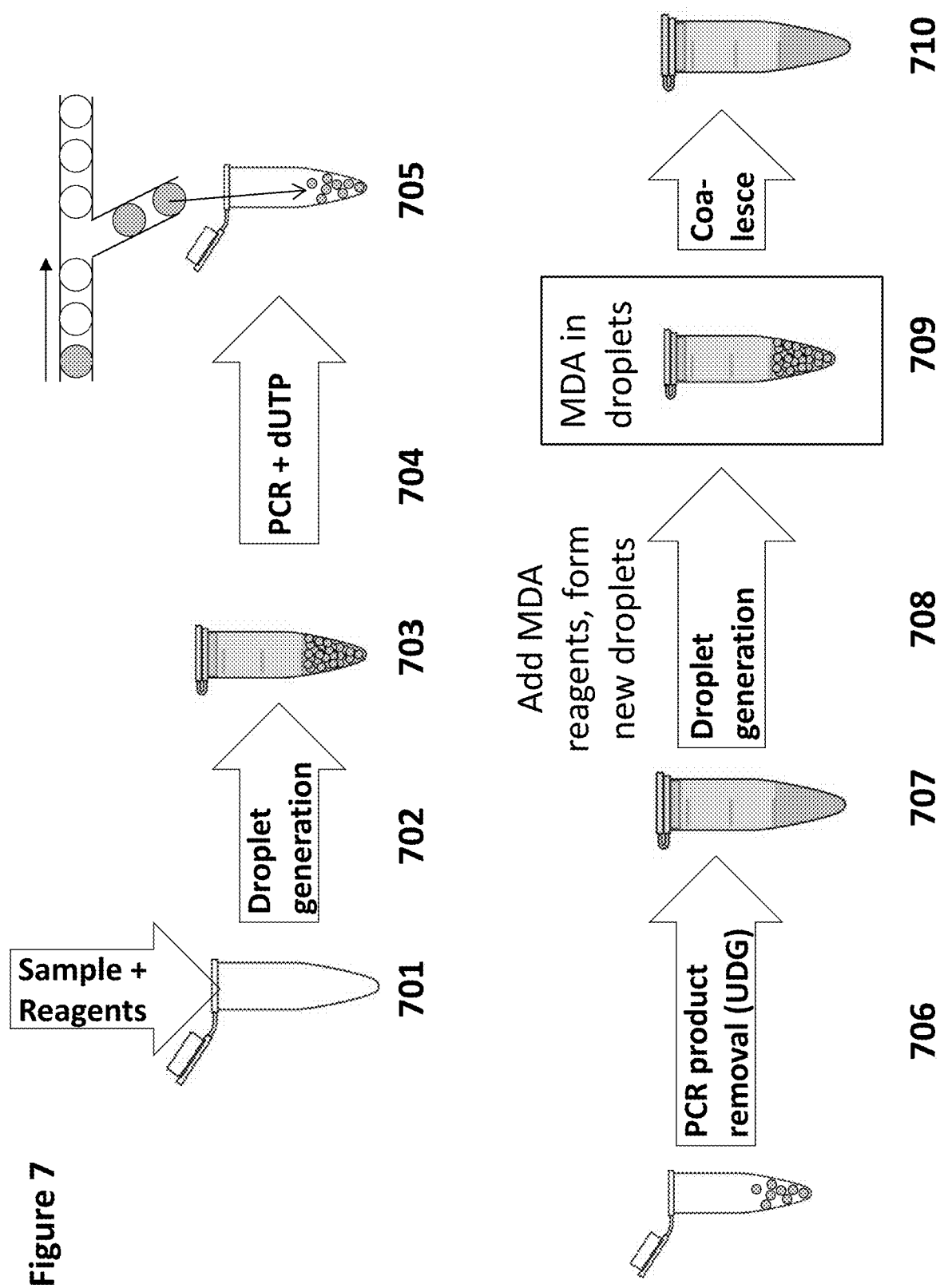

FIG. 7: Outline of a scheme for performing PINSswift as described in example 3.
701: A DNA sample containing the DNA target and reagents for PCR are mixed.
702: Components required for droplet generation are added to the mixture.
703: Droplets containing the DNA sample and reagents are generated.
704: PCR amplification of a portion of the target DNA molecule using dUTP in the reaction mixture.
705: Positive droplets containing the target DNA molecule are detected based on fluorescence generated in PCR, selected and sorted in a microfluidic chip.
706: The collected, sorted positive droplets are coalesced, UDG is added and the reaction is incubated at 37° C. to remove the PCR product used for detection and then the reaction is terminated by incubation at 95° C. resulting in sample 707.
708-709: Reagents for Phi polymerase amplification are added to the water phase, emulsion oil is added, the sample is vortexed and the emulsion is incubated at 30° C., and the droplets are coalesced to generate sample 710.

Figure 8:
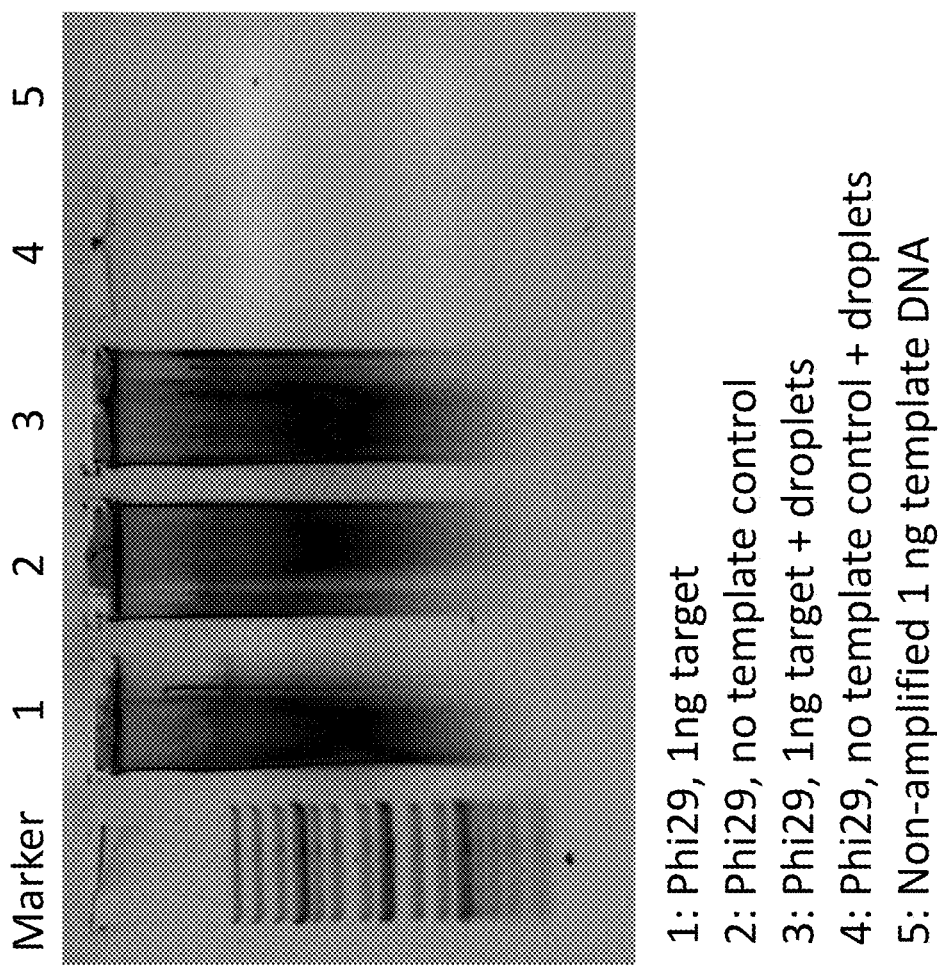

FIG. 8: An agarose gel (stained for DNA) comprising the size-separated products of Phi29 amplification of an E. coli DNA template. The Phi polymerase amplification reaction mixture with or without template was prepared, and the reaction was allowed to proceed; or the reaction mixture was converted to droplets and then the reaction was allowed to proceed; 1) 1 ng/µL E. coli DNA template, no droplets, 2) No DNA template, no droplets, 3) 1 ng/µL E. coli DNA template, reaction in droplets, 4) No DNA template, reaction in droplets, 5) 1 ng/µL E. coli DNA template, no droplets, no Phi29 polymerase. Marker: 1 kb+DNA ladder as size marker.

Figure 9:
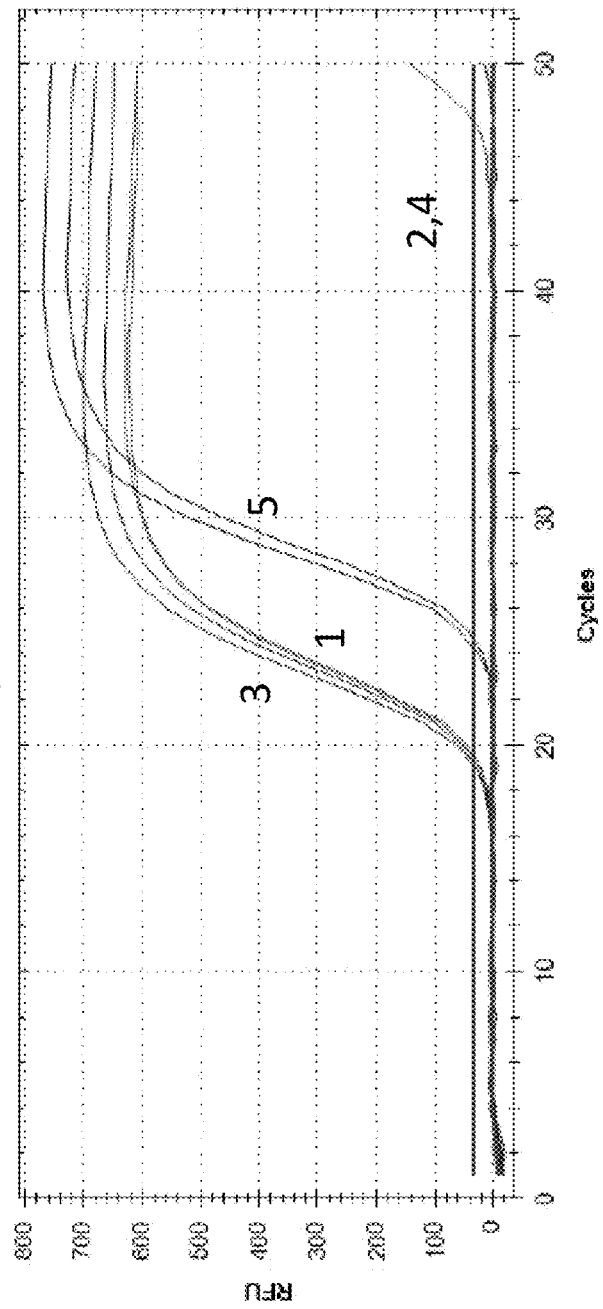

FIG. 9: Quantitative PCR specific detection and quantitation of the E. coli DNA produced by Phi polymerase amplification of an E. coli DNA template (analyzed samples correspond to the products of Phi polymerase amplification size separated on the agarose gel shown in FIG. 8. The templates used for qPCR were the products of: 1) 1 ng/µL E. coli DNA template amplified by Phi polymerase, no droplets (B01-B02), 2) No template control amplified by Phi polymerase, no droplets (B03-B04), 3) 1 ng/μL *E. coli* DNA template amplified by Phi polymerase in droplets (B05-B06), 4) No template control amplified by Phi polymerase in droplets (B07-B08), 5) Positive *E. coli* DNA control (B09-10).

DETAILED DESCRIPTION OF THE INVENTION

Detection and characterisation of a target DNA fragment (or molecule) in a complex mixture of DNA fragments (or molecules), particularly a low copy number target molecule, requires a sensitive detection method combined with methods for purification and analysis of the target DNA. It is known in the art, that the most sensitive PCR reactions are obtained when the DNA fragment is short, such as 100-250 base pairs. Long range PCR, designed to amplify DNA fragments that are longer than 250 base pairs, for example 500 to 5000 base pairs in length, are not capable of detecting low amounts of target DNA fragment present in a sample of mixed DNA fragments containing high amounts of background DNA. Similarly, hybridization based methods require the sample to be relatively pure to avoid non-specific hybridization. The best described ways of obtaining sequence information from a sample of mixed DNA fragments or a very dilute sample has been based on sequencing the entire mixture of DNA fragments by e.g. next generation sequencing methods, and, although the cost of next generation sequencing is rapidly decreasing, the cost of sequencing thousands of genomes is still high. However, even this approach has its limitations, since the PCR amplified DNA fragments themselves yield short sequences (100-250 base pairs) that must be further assembled to determine translocations, insertions or deletions or polymorphisms that may be detected over long range regions of DNA fragments of previously unknown sequence.

The in vitro method for enriching for one of more target DNA molecule from a sample of mixed DNA molecules according to the present invention, employs DNA detection methods (such as PCR) solely for the purpose of identifying DNA molecules (fragments) that comprise the one of more target DNA molecule. Since short DNA sequences are sufficient to identify the target DNA, the present method takes maximum advantage of the most sensitive forms of PCR for detection of a DNA target molecule in a complex DNA mixture. The detection reaction is performed in droplets prepared from the sample of mixed DNA molecule combined with detection reagents. This has the advantage that the reaction conditions and reagents are optimised for the detection step, which is particularly advantageous for PCR-based detection with respect to $Mg^{++}$ ion concentration (which is 10 fold lower than the optimal $Mg^{++}$ ion concentration for Phi polymerase general amplification), and target-specific primers. Since the droplet size is typically small (1-100 μm in diameter), the total volume of the combined droplets comprising target DNA will be small relative to the subsequent amplification reactions, allowing an optimisation of reaction conditions for the subsequent steps of the method.

The characterisation of one of more target DNA molecule detected in a sample of mixed DNA molecules requires a sufficient number of copies of the detected molecule. The enzyme Phi29 polymerase, derived from the bacteriophage Φ29, can be used for whole genome amplification (WGA). Using a method of multiple displacement amplification (MDA), fragments tens of kilobases in length can be produced using the Phi29 polymerase together with non-specific hexameric primers that anneal at intervals along a DNA template. However, it is known that Phi29 polymerase requires a certain amount of input DNA to function in an amplification reaction. Main suppliers of Phi29 polymerase such as Qiagen and Fidelity systems state in their product specifications that the minimum input for the Phi polymerase reaction is 1 ng or higher (www.qiagen.com/dk/products/catalog/sample-technologies/dna-sample-technologies/genomic-dna/repli-g-single-cell-kit, www.fidelitysystems.com/phi29_hexamers.html).

Additionally, locus underrepresentation and background products have been reported when low amounts of DNA input material are used. The method according to the invention requires a polymerase that is capable of amplifying ≤less than 300 fg of DNA (corresponding to 5565 linear DNA molecule of 50,000 nucleotides). This is more than 3000 fold lower than the reported template requirements of the Phi29 polymerase. Surprisingly, the Phi29 polymerase was found to provide an effective amplification of detected and selected DNA molecules using the method of the invention, even when the input DNA was below 5 fg of DNA. As illustrated in Example 1, as little as 1.7 fg of DNA (corresponding to 1.3 linear DNA molecules of 50,000 base) were effectively amplified using Phi29 polymerase. Thus, not only was Phi29 polymerase unexpectedly found to amplify such low amounts of DNA molecules but additionally it was unexpectedly found that the general amplification reaction can be performed in a very small volume, such as droplet (1-100 μm in diameter). Where the general amplification volume is performed in such droplets, the degree of bias is further reduced, since the production of non-specific amplification products (such as those derived from amplification of non-specific hexameric primers and/or contaminating DNA not originating from the sample of mixed DNA molecules) is minimised. Surprisingly, the present invention reveals that amplification of contaminating DNA by Phi29 polymerase in a sample can be eliminated by performing the general amplification reaction of DNA molecules in droplets, in particular droplets having a volume of about 5 pL (see Example 4).

The present invention pertains to an in vitro method in which the concentration of a specific target DNA molecule is increased relative to the concentration of total DNA in a sample, by 1) dilution of a sample into multiple sub-compartments such as droplets (separation) containing reagents for detection of specific target, 2) detection of the specific target sequence within the droplets and, 3) physical selection of droplets containing the target sequence (selection), 4) addition of chemicals for general DNA amplification to the selected DNA containing the target sequence, 5) general amplification of the selected DNA containing the target DNA molecule.

The invention is based on the principle that, if only a fraction of the droplets contain the target DNA molecule, the concentration of the target DNA molecule relative to total DNA is higher in these droplets, compared to the concentration in the original sample. The fraction of droplets containing the target determines the degree of enrichment; if the fraction is low, the enrichment is high (FIG. 3).

In the context of the present invention, the presence or absence of the target DNA molecule in a sample or a dilution thereof or droplet, is defined by the presence of detectable target molecule in the sample, or a dilution thereof, or droplet using the selected method of detection (e.g. PCR).

The target can be further enriched by further rounds of selection (as above), until it can be sequenced by standard methods such as Sanger sequencing, sequencing by synthesis, Pyrosequencing or similar detection of DNA sequence or by PCR, hybridization or other detection assays, or it can be used directly from the first round of selection.

Droplets amplified and sorted according to the invention contain DNA fragments of 5-100 kb containing the sequence used for identification.

Surprisingly little prior sequence information is needed for the enrichment according to the invention. In comparison to current enrichment technologies, only approximately 40 nucleotide base pairs of specific target information is required as compared to at least 5000-8000 and 300 base pairs respectively for hybridization based and long range PCR based methods respectively (FIG. 1). The small amount of sequence information needed in combination with the large DNA fragments obtained from enrichment makes it possible to sequence into regions of a given DNA fragment that are only partially known. These regions can contain unknown translocations, insertions or deletions or they can be regions comprising polymorphisms.

The method of the invention is surprisingly efficient, whereby the extent of DNA sequencing can be reduced by a factor of more than 1 billion for 5 multiplexed DNA targets by three rounds of PINSswift or a factor of 25 million for one target sequence using two rounds of PINSswift (FIG. 2).

I: Partitioning Isolation of Nucleotide Sequences (PINSswift)

The essential steps of the PINSswift method are further described below:
a) Providing a DNA Sample Potentially Comprising one or more Specific Target DNA Molecule and Reagents for Detecting the Presence of the Target Molecule (401)
A sample of mixed DNA molecules potentially comprising a target DNA molecule, is selected for performing PINSswift. One or more nucleotide sequences of at least 10 (or 15, more preferably 40) unique nucleotides located within the target DNA molecule is selected for screening and detecting the DNA molecule by a desired method, such as PCR detection, DNA detection with hybridization probes or similar. The target DNA molecule is typically larger than 500 base bairs, such as between 2000 and $10^8$ base pairs, preferably between 2,000 and 200,000 base pairs, more preferably between 10,000-100,000 base pairs. A target DNA molecule may contain more than one unique nucleotide sequence, each sequence corresponding to a given genetic marker, for example one genetic marker sequence diagnostic of an infectious agent and a second marker diagnostic of an antibiotic resistance gene. Typically, the frequency of the target DNA molecule in the sample of mixed DNA molecules is less than $10^{-2}$, it may for example lie between $10^{-3}$ and $10^{-9}$, or for example between $10^{-4}$-$10^{-7}$, or even less than $10^{-11}$ (calculated as base pairs of target sequence divided by base pairs of total DNA in the sample). Prior to amplification, the liquid sample of mixed DNA molecules is serially diluted by a desired number of dilutions until each droplet in the subsequent droplet formation step contain less than 0.01 target DNA molecule on average, preferably less than 0.001 or even more preferably less than 0.0001 specific target DNA molecule on average. Typically, the total number of droplets formed in step b) of the method is from between $5\times10^3$ and $1\times10^{10}$, or from between $2\times10^4$ and $1\times10^7$, or between $5\times10^5$ and $5\times10^6$. Thus, if the liquid sample of mixed DNA molecules is separated into 100,000 droplets, on average the target DNA molecule will be present in less than 1,000 of these droplets, preferably less than 100 of these droplets, even more preferably less than 10 of these droplets. The presence or absence of the target DNA molecule in a droplet is defined herein as the presence or absence of detectable target DNA molecule when employing methods for specific detection of the target DNA molecule, such as those exemplified in the present application. This dilution is performed to ensure target enrichment; if the average number of droplets containing target is low, the frequency of target relative to non-target molecules within the droplet is high. The frequency and abundance of the target DNA molecule in the mixed DNA sample may be determined by DNA concentration measurement, PCR, real time PCR, by hybridization based assays or by assays detecting an RNA or protein product of the target sequence. Reagents for PCR detection include a PCR polymerase (e.g Taq polymerase), a $Mg^{++}$ concentration of 1.5-2.5 mM in 1× Standard Taq Reaction Buffer, and 200 μM dNTPs of each deoxynucleotide, that is typically optimal for most PCR products generated with Taq DNA Polymerase. Oligonucleotide primers, generally 20-40 nucleotides in length, whose sequence is capable of specifically binding to the 5' and 3' ends of the known sequence of the target DNA molecule.
b) Formation of a Multiple of Droplets Containing said DNA Sample each Containing less than 0.5, Preferably less than 0.25 or even more Preferably less than 0.1 Specific Target DNA Molecule on Average (403).
Droplets containing diluted sample DNA and reagents necessary for specific detection of target DNA are generated using any method of droplet generation to isolate target DNA sequences in closed compartments. Suitable methods for droplet generation include active methods such as acoustic energy ejected droplets, dielectrophoresis (DEP) and electrowetting on dielectric (EWOD), and passive methods such as shear focusing [1], or T-junction, x-junction and flow focusing [2], vortexing, shaking, and sonication. In addition to droplets, the general amplification can occur in other microvolume compartments, such as reaction chambers in microfluidic chips.
c) Specific Detection of Droplets Containing said Specific Target DNA (404)
Following droplet generation in step b) the droplets are screened for the presence of the target DNA molecule using the desired detection technique. In at least one or more screened droplets that are shown to contain the target DNA molecule, the frequency of the target DNA molecule will be increased compared to its frequency in the sample of mixed DNA molecules in step (a) According to a first embodiment of the invention, the average total number of DNA fragments per droplet (e.g. single target in a sample, such as one gene from a human genome): is from 1 to 1,000, or 2 to 100, or 3 to 10 DNA fragments. Where there is on average only one DNA fragment per droplet, then the positive droplets will on average comprise the target DNA molecule in pure form. According to the second embodiment of the method, all droplets formed in step b) of the method comprise mixed DNA and the increase in frequency, obtained by selection of the positive droplets is typically between 0.1×(total number of DNA-containing droplets)×(number of droplets with target DNA)$^{-1}$ and 10×(total number of of DNA-containing droplets)× (number of droplets with target DNA)$^{-1}$.

The number of droplets containing target is typically between 5 and 1000 per target sequence. The total number of droplets is at least 5,000, but typically greater than 20,000 and often greater than 500,000.

The presence of the target DNA molecule in the droplets may be determined by PCR including qPCR, by hybridization based assays or by assays detecting an RNA or protein product of the target sequence. The reagents for specific detection may contain dUTP to make it possible to selectively inactivate the DNA amplified in the detection step using UDG at a subsequent step.

d) Physical Selection of Droplets Containing said Specific Target DNA (406)

Based on the detection of target DNA in step c) droplets are sorted into at least two different streams. When more than one specific target is detected in step c), the droplets may be sorted into 3, 4, 5 or more streams. In the stream containing droplets wherein the target is detected, the target is enriched as compared to the sample of mixed DNA molecules in step a).

e) General Amplification of DNA Molecules from Selected Droplets Containing Specific Target DNA Molecules (406)

DNA from selected droplets containing specific target DNA, and wherein total amount of DNA is less than 300 fg, is amplified using any method of total DNA amplification to increase the abundance of the DNA in each sample. A suitable general amplification method is Multiple Displacement Amplification (MDA)[4]. In a preferred embodiment the enzyme employed for performing the general amplification is Phi29 polymerase; preferably the general amplification enzyme consists of Phi29 polymerase, whereby general amplification does not require additional polymerases. It may be necessary to add reagents for general amplification by breaking, mixing, or fusing droplets or to break emulsion by applying force such as centrifugation and/or sonication.

In one embodiment, droplets, generated from a liquid sample comprising the selected coalesced droplets containing specific target DNA and the reagents for general amplification, are prepared using any method of droplet generation to isolate target DNA sequences in closed compartments (see above). General amplification then takes place in the generated droplets (see FIG. 5). Preferably the general amplification reaction is performed in droplets that are at least 1 μm in diameter on average (corresponding to an average droplet volume of at least 0.00052 pL; allowing the formation of ≤1.9 billion droplets/μL general amplification reaction mixture). Preferably the droplets have a diameter of from 2 to 20 μm on average (corresponding to an average droplet volume of 0.0042 pL; with the formation of 240 million droplets/μL; up to an average droplet volume of 4.2 pL; with the formation of 240,000 droplets/μL). Accordingly, where the volume of the general amplification reaction is at least 5 μl, then the general amplification reaction will be performed in at least 1.2×10$^6$ droplets; and up to a maximum of 1.2×10$^9$ droplets for each 50 μl of reaction mixture. Following amplification, all droplets are then coalesced, and the target DNA molecules may then be further detected, selected and amplified in a subsequent cycle of steps a) to e).

Optional Steps:

f) Inactivating, Degrading or Removing DNA Produced for Specific Detection of Target DNA When the enriched target DNA molecule is used for further rounds of PINSswift or other applications where the presence of the detection product interferes with these further processing, the amplification of DNA in the detection step c) can be performed using dUTP in place of one of the deoxyribonucleotide (dNTPs), where the product may then be optionally selectively degraded, inactivated or removed. This inactivation may be performed using an enzyme such as Uracil-DNA glycosylase, also known as UNG or UDG.

g) Repeating Steps (a) to (e)

Using the droplets containing enriched target DNA molecules obtained in (e) in a new step (a), the target DNA molecules may be further enriched.

h) Amplifying the Enriched Sample

Using the enriched amplified target DNA molecules obtained in (e), the target DNA molecules may be further amplified using a general amplification such as MDA or a specific amplification such as PCR. For example, further amplification may be performed by collecting the water phase from the coalesced droplets obtained following general amplification in step e); adding reagents for general amplification to the water phase to form a reaction mixture; generating new droplets from the reaction mixture, and incubating the droplet emulsion at 30° C.

Scheme for Performing PINSswift

The scheme is outlined in FIG. 4. (401): Determine the concentration of target DNA molecules in the original DNA sample. Dilute the sample until the expected average number of droplets containing a target molecule (positive droplets) is less than 0.5. If only one target is enriched, the average number of positive droplets should be smaller resulting in a greater enrichment. Ideally, the entire sample of droplets should contain 2-100,000 positive droplets per specific target, preferably 5-10,000 and more preferably 20-100. When two different specific targets such as two different genes are to be enriched from the same sample, the ideal number of positive droplets is two times higher. If more than one sequence variant of the target is present, each variant counts as a separate target DNA molecule. Also, if a target DNA molecule is long, such as longer than 20,000 base pairs, more than one properly spaced nucleotide sequence for detection of specific target may be used. Each of these nucleotide sequences counts as separate DNA molecules. The correlation between number of targets, the average number of positive droplets and the resulting enrichment after PINSswift is shown in FIG. 3 using an example of one round of PINSswift, 20,000 droplets and 10 positive droplets per target.

The enrichment may be higher or lower than the expected enrichment of FIG. 3 due to bias of this amplification step. In our experience the resulting enrichment may be at least two fold higher. Also, if a larger number of droplets such as one million droplets are used, this will result in a greater enrichment. To achieve a great enrichment a smaller droplet size is therefore typically preferable. A typical size of the droplets may be less than 100 μm in diameter, such as 1-100 μm, 5-50 μm or preferably 10-30 μm. The droplets may also be of varying sizes within the same sample.

The diluted target DNA molecules are mixed with reagents suitable for detection of the target sequences in the sample. If detection is performed using PCR, these reagents may include a polymerase, target specific primers, probes such as Taqman probes, molecular beacons, or scorpion probes, SybrGreen, nucleotides, and salts.

Droplets containing mixed DNA and reagents for detection are now generated (403)

If detection is performed using PCR; the droplet sample is transferred to a PCR apparatus and PCR amplification is performed and the droplets are then sorted according to the presence (positive) or absence (negative) of the target molecule. Where fluorescence labelled oligonucleotides are used, the presence of the target molecule can be detected by the fluorescence of the droplets (404 and 405).

The selected and sorted droplets will contain a small amount of target DNA molecules such as 2-1000 molecules and amplification of said molecules is therefore necessary before the DNA can be used for downstream applications e.g. DNA sequencing. Due to the small amount of DNA, it may not be possible to generally amplify the DNA using standard procedures. Methods to improve the amplification include repeated steps of amplification and re-amplification and combinations of amplification in droplets and standard amplification (in one reaction, excluding droplet formation).

Determine the abundance of the target DNA molecule. If this is sufficient for analysis such as sequencing, the selected sample may be used directly; otherwise additional rounds of PINSswift can be applied.

When it is necessary to perform further rounds of enrichment, it may be preferred to degrade or remove the DNA generated in the detection step. It may be preferred to use dUTP in the PCR reagents. The MDA reaction is then performed using standard dNTPs. After detection and physical selection of droplets, the DNA generated in PCR can be degraded and the treated sample can be used for an additional round starting with dilution, detection and physical selection.

When a sufficient enrichment is reached using PINSswift, the droplets are fused (also termed coalesced or demulsified). The enriched DNA may also be further purified and may be further amplified using general or specific amplification such as MDA and PCR respectively.

The PINSswift procedure employs general amplification to the target DNA molecule after it has been sorted. This has several advantages over a procedure where the DNA is generally amplified in droplets before detection and sorting including 1) the chemicals and enzymes needed for general amplification do not need to be present in the detection step, and 2) as the volume of the sorted droplets is small, the detection chemicals will only have minimal influence on the general amplification step. When general amplification is performed using Phi29 polymerase in a process where the DNA is amplified in droplets before detection, the polymerase will degrade oligonucleotides to be used for detection thereby preventing correct identification of droplets containing target DNA molecule. Also, when PCR is subsequently used for detection, the reaction conditions are not optimal for general amplification, and the general amplification can be inhibited. In a process employing general amplification in droplets before detection, the detection chemicals could alternatively be added to the droplets after general amplification thereby avoiding the problems of incompatibility between the detection and general amplification reactions. However, this complicates the process by requiring a droplet fusion step. By performing general amplification after detection and sorting, PINSswift achieves efficient detection while keeping a good performance of the general amplification and without adding the complexity of droplet fusion.

II: Multiplex PINSswift

PINSswift can be adapted to perform multiplex PINSswift. Multiplex PINSswift employs additional features that are designed to detect a 2nd consecutive sequence of at least 10 (or 15, more preferably 40) nucleotides in the sample of mixed DNA molecules analysed, by amplification of this 2nd consecutive sequence with sequence specific primers to generate a 2nd target DNA molecule. If several droplets show specific detection (e.g. by fluorescence signal) from both the 1st and 2nd consecutive sequence then they have a high probability of being located on the same MDA-amplified target DNA molecule.

In addition to providing information concerning co-localisation of targets, multiplex PINSswift provides simultaneous purification of up to thousands of different target molecule, each comprising more than 5,000 base pairs. Separate detection molecules can be provided to separate droplets or can be added as a mixture.

III Samples Analysed by PINSswift and Multiplex PINSswift

III.i Sample of Mixed DNA Molecules

PINSswift may be applied to a sample of mixed DNA molecules that may comprise a target DNA molecule. A sample of mixed DNA molecules comprises a population of DNA molecules (e.g. chromosomal DNA molecules or plasmid DNA molecules) where the individual DNA molecules within the population differ by at least one nucleotide within a known consecutive sequence of at least 10 (or 15 or more preferably 40) nucleic acid base pairs in their DNA, such that a target molecule comprising the known consecutive sequence differs from, and can be distinguished from, non-target molecules in the sample. The sample of mixed DNA molecules may additionally comprise single stranded RNA or DNA polynucleotides. The population of DNA molecules in the sample of mixed DNA molecules comprises the target DNA molecule.

The target DNA molecule can be in linear or circular forms. Circular DNA can occur naturally or can be obtained by cloning DNA into plasmids, fosmids, cosmids, BAC clones, or generated by ligation or through Cre/LoxP mediated recombination.

A target DNA molecule comprises one or more known consecutive sequence of at least 10 (or 15 more preferably 40) unique nucleic acid base pairs (or nucleotides). A target DNA molecule can be selected from a sample of mixed DNA molecules, by selecting for a target DNA molecule comprising this consecutive sequence of at least 10, 15 or 40 nucleic acid base pairs (or nucleotides). The target DNA molecule can also be selected from the sample of mixed DNA molecules, by selecting for a target DNA molecule comprising at least two consecutive sequences of at least 10 (or 15 more preferably 40) nucleic acid base pairs (or nucleotides), wherein the two consecutive sequences are comprised within a DNA molecule of 50 to 100,000 nucleic acid base pairs, preferably 150 to 3,000 nucleic acid base pairs, more preferably 150 to 1500 nucleic acid base pairs.

Typically, the frequency of the target DNA molecule in the sample of mixed DNA molecules is less than $10^{-2}$, it may for example lie between $10^{-3}$ and $10^{-9}$ (calculated as base pairs of target sequence divided by base pairs of total DNA in the sample). For illustration purposes, the sample could be DNA from a human swab and the target DNA could be a region of 30,000 base pairs containing a specified gene. In this case, the frequency of the target DNA molecule is 30,000 divided by approximately 3 billion base pairs (the human genome) which equals $10^{-5}$.

The method of the invention is particularly suitable where the frequency of the target DNA molecule in the sample of mixed DNA molecules is less than $10^{-2}$. The method of the invention is also suitable where the frequency of the target DNA molecule in the sample of mixed DNA molecules is less than $10^{-3}$, $10^{-4}$, $10^{-5}$, $10^{-6}$, $10^{-7}$, $10^{-8}$, $10^{-9}$, $10^{-10}$, or $10^{-11}$. In many instances, the sample of mixed DNA molecules will be derived from a cell population comprising genomic DNA, while in other instances the sample may be derived from samples where the DNA molecules are of diverse origin, such as environmental samples.

Irrespective of its source, the frequency of the target DNA molecule is defined as the number of specific target DNA base pairs divided by the number of total base pairs in the sample. The frequency of the target DNA molecule in the sample of mixed DNA molecules is determined by making a dilution series in triplicate, detecting the presence or absence of target and determining the number of targets using, for instance, most probable number methods. The frequency of the target molecule can also be determined using qPCR or digital droplet PCR [3]. The concentration of DNA is measured and the number of total genome equivalents is determined by dividing this concentration by the average molecular weight of the genome.

III.ii Source of the Sample of Mixed DNA Molecules

According to one embodiment of the present invention, the target DNA molecule is derived from the genome of a cell, where the genome may be either chromosomal or extra-chromosomal DNA, or from DNA present outside of a cell such as from a virus or cell free DNA. Further, the target DNA molecule may be derived from a cell, where the cell is selected from amongst a microbial cell, a plant cell, an animal cell, a protist cell, a fungal cell, or a mammalian cell. The mammalian cell may be a human cell. The microbial cell may be a bacterial cell, a yeast cell or a fungal cell. Furthermore, the target DNA molecule may be derived from a fungal mycelium or fungal spores.

When the target DNA molecule is derived from one or more cell, the cell(s) may be part of a multicellular tissue or multicellular organism.

Furthermore, the target DNA molecule may be derived from one or more viral particles, where the virus has an RNA or DNA genome. Alternatively the target DNA molecule may be derived from a host genome comprising integrated DNA derived from a virus. The target DNA molecule may also be derived from a bacteriophage.

Irrespective of the derivation of the target DNA or RNA molecule, the target DNA or RNA molecule is present in a sample of mixed DNA molecules, where the mixed DNA molecules may be derived from a sample collected from the environment, for example a sample of soil, water or air. Alternatively, the sample may be derived from a multicellular organism, such as a mammal, for example an animal or a human subject. When the sample is derived from a mammal, the sample (for example a biopsy) may be derived from a body fluid (e.g. blood, plasma, serum, lymph and urine), from faeces or from a body tissue or organ. The multicellular organism from which the sample is derived may be a living or may be a dead organism.

III.iii Preparation of the Sample of Mixed DNA Molecules

The sample of mixed DNA molecules comprising the target DNA molecule may be prepared from a sample collected from nature or from an organism (e.g. a biopsy). Methods for selective extraction of DNA molecules are known in the art [4]. When the target DNA molecule is derived from a cell, the step of cell disruption or cell permeabilisation is normally required in order to release total nucleic acid molecules (including DNA or RNA) from a cell, this step preceding the subsequent step of selective extraction of DNA molecules.

Where the target DNA molecule is derived from an RNA genome, the RNA genome or parts thereof are first reverse transcribed to provide a cDNA molecule, where the nucleotide sequence of the cDNA corresponds to (is a reverse transcript of) the RNA genome.

Before generation of droplets, a compound such as a protein, or a compound comprising a DNA or RNA fragment, such as a DNA fragment coupled to a protein, may be bound to the target nucleotide in order to enable or facilitate subsequent detection. Unbound compounds may be washed from the sample before generation of droplets. Useful proteins include antibodies, single-chain variable fragment and enzymes. Useful compounds include DNA binding proteins such as regulatory proteins and histones.

The DNA sample may be circularized before the generation of droplets. Some general amplification methods, including the Phi polymerase catalyzed MDA reaction, are more efficient on circular templates. By circularizing the template, the DNA from the original nucleotide sample may therefore be favoured over non template reaction or templates stemming from the detection reaction and bias against target can thereby be reduced.

The sample may be diluted before formation of droplets. If for example 1 million droplets are used for the enrichment of a gene from human chromosomal DNA 100 pg human DNA may be used to obtain 30 copies of target DNA molecule in the 1 million droplets. As a copy of the human genome contains approximately 100,000 fragments of 30,000 base pairs, each droplet may therefore contain an average of 3 fragments. The approximately 30 droplets containing the target DNA molecule will therefore also contain non-target fragments. If the DNA is sequenced after the enrichment is finalized, the non-target fragments may also be sequenced but, as the non-target fragments are likely to be different from each other, the sequence of the target DNA molecule is clearly distinguishable. For more complex samples such as a low copy virus in a human sample, the number of non-target fragments per target fragments in a positive droplet may be even higher such as higher than 100:1 or 10,000:1.

The total number of target DNA molecules is typically between 5 and 1,000, such as 5-100,000. When only one variant of a target DNA molecule is needed, the preferred number of total target DNA molecules added to the droplets is low such as 20-100 to achieve a high degree of enrichment. When several different variants are needed, such as in the analysis of inhomogeneous tumour DNA, a higher number of total target DNA molecules may be preferred such as 100-10,000.

III.iv Generation of Droplets

Methods of the invention include forming multiple droplets where the droplets each contain less than 0.01 specific target molecules on average. In the preferred embodiment the distribution of specific target molecules follows Poisson distribution. Some droplets may contain non-target molecules present at 10 fold or higher concentrations as compared to the target molecule, while other droplets may contain only the target molecule.

Generally, droplets can be formed by a variety of techniques such as those described in [5-7]. Methods of the invention may involve forming a two-phase system comprising aqueous droplets surrounded by an immiscible carrier fluid. In a preferred embodiment, the aqueous sample within the droplet is prepared by preparing a mixture suitable for specific detection of target DNA molecules containing sample DNA and e.g. a polymerase, primers, probes and buffer solutions.

The resulting mixture is used as the aqueous sample in two-phase liquid droplet formation using two immiscible liquid phases. Aqueous droplets are either generated in an apparatus having means for creating a vortex/turbulence in a sample comprising two immiscible liquid phases in controlled environments, creating droplets of liquid (phase 1) in a 2nd phase liquid by controlling the mechanical parameters and thereby also the liquid volume of each generated droplet or by a means for extruding droplets of one liquid phase in a 2nd immiscible liquid phase, where the so formed droplets remain discrete and wherein the volume of the droplet is controlled by the diameter of the means for droplet extrusion.

The carrier fluid is one that is immiscible with the sample fluid. The carrier fluid can be a non-polar solvent, decane, fluorocarbon oil, silicone oil or any other oil (for example mineral oil).

In certain embodiments, the carrier fluid contains one or more additives such as agents which increase, reduce, or otherwise create non-Newtonian surface tensions (surfactants) and/or stabilize droplets against spontaneous coalescence or contact.

IV Methods of Detecting the Target Sequence

Methods of the invention further involve detection of the target nucleic acid molecule within the droplets containing target DNA molecules. In certain embodiments the detection involves amplification of a part of the target molecule. The amplification reaction, that is suitable for amplifying nucleic acid molecules, includes polymerase chain reaction, or nested polymerase chain reaction including or excluding probes such as Taqman probes, Scorpion probes, Molecular Beacon probes, Padlock probes, Molecular inversion probes and any other probe that functions by sequence specific recognition of target DNA molecule by hybridization and result in increased fluorescence on amplification of the target sequence.

Methods according to the invention also include methods wherein detection is based on fluorescence from optically labelled probes such as fluorescently labelled probes wherein the target is not amplified. In this case, the DNA is denatured e.g. by increasing temperature to around 95° C. and the probe is subsequently allowed to anneal to the target, resulting in activation of the probe or probes. Such optically labelled probes can be Molecular Beacons, where a single-stranded bi-labelled fluorescent probe is held in a hairpin-loop conformation of around 20 to 25 nt by a complementary stem sequences of around 4 to 6 nt. Due to the loop-structure the desired fluorochrome attached to one end of the sequence is in close proximity of the light quencher attached to the other end. When the structure is released during denaturing and then re-annealed, the probe anneals to an amplified target. When annealed, the hairpin structure is no longer maintained, and the quencher no longer quenches emitted light from the fluorochrome. The optically labelled probes can also be FRET (fluorescence resonance energy transfer) probes.

The specific target sequence may also be detected using nucleic acid stains such as cyanine dyes.

V Methods of Physically Selecting Droplets Based on Presence of the Target Sequence To selectively separate droplets comprising a detectable target DNA molecule from droplets wherein the target is not detected, a variety of different methods for physical selection of droplets or droplet sorting can be employed including steering, heating, electro-wetting, magnetic activated sorting, acoustic waves [6], and dielectrophoretic sorting [8]. Such physical selection can be carried out using an apparatus with means for receiving droplets of an aqueous liquid that are suspended in a 2nd immiscible liquid (e.g. droplets from specific detection step), and means for passing each droplet past a detection unit capable of detecting a component in said droplet, and means for addressing said droplet for delivery to a selected compartment as determined by the presence or absence of the detectable component and means for delivering said droplet to the selected compartment.

VI Methods of General Amplification of DNA Suitable for PINSSWIFT

A range of different approaches have been suggested for general amplification of DNA, such as randomly degenerate primed PCR, linker ligation PCR, or, Degenerate Oligonucleotide Primed (DOP) PCR and Multiple Displacement Amplification (MDA). MDA is reported to be efficient in performing whole-genome amplification (WGA) of even small amounts of DNA (but with a lower limit of circa ing). Compared with more traditional PCR-based WGA methods, MDA generates DNA molecules with a higher molecular weight, having better genome coverage. MDA employs a strand displacement polymerase that possesses two enzymatic activities: DNA synthesis (polymerase) and an exonucleolytic activity that degrades single stranded DNA in the 3'- to 5'-direction, as exemplified by bacteriophage phi29 polymerase, that belongs to eukaryotic B-type DNA polymerases (UniProtKB/TrEMBL: Q38545). Other useful polymerases include Bstl polymerase. The amplification may be performed in droplets to increase the local concentration of DNA. In some embodiments, the amplification is performed at around 30° C. for four hours, preferably less than one hour.

As the amount of target DNA molecule from the detection and sorting step may be as low as five or fewer molecules, typical general amplification reactions will either produce no product or produce background reaction (no template reaction).

It was found that background reaction is prevented and sensitivity is increased when amplification is carried out in droplets such as water-in-oil droplets of 1 pL to 1 nL thereby making PINSswift possible at low numbers of DNA target molecules such as less than 100 molecules corresponding to approximately 3 fg of DNA. The reaction is improved even when the droplets are of variable sizes such as droplets produced by vortexing. The droplets are subsequently coalesced (also termed demulsified) either in one step or gradually to form a solution containing the enriched target DNA molecules.

VII Methods of Removing the Detection Signal Molecules after Physically Selecting the Droplets After physically selecting the droplets based on the presence of the specific target sequence, it may in some cases be necessary to remove a detection signal, such as a PCR product. Several methods for removing such signals are known in the art. If dUTP has been used in the detection reaction, the detection molecule may be removed using uracil-DNA N-glycosylase [9]. Alternatively, as the molecules produced by general amplification are significantly longer than the detection molecules, the detection molecules can be separated using methods based on size separation such as size exclusion based on differential binding affinity of small and large DNA to silica particles [10]. Such silica surfaces have limited binding efficiency to DNA fragments smaller than 100 bp, and consequently only DNA fragments smaller than 100 bp will efficiently be discarded, when silica based purification in applied. In some applications, however, it may not be necessary to remove the detection molecule. For instance, since Phi polymerase and some other polymerases have low activity on DNA molecules shorter than 1000 base pairs, it may not be necessary to remove the detection molecule if the step following PINSswift enrichment is a general amplification since the detection molecule will only be amplified to limited extent, if at all amplified, compared to the actual targeted larger DNA molecule.

VIII Sequence Determination of the Target DNA Molecule

When a target DNA molecule is sufficiently enriched and generally amplified, the the nucleotide sequence of the molecule including the target nucleotide sequence can be determined. The enriched target DNA molecule can be sequenced using e.g. Sanger sequencing, Emulsion PCR, Shotgun sequencing, SOLID sequencing, bridge PCR, Ion Torrent sequencing, Polony sequencing, Pyrosequencing, Sequencing by synthesis, DNA nanoball sequencing, Heliscope single molecule sequencing, Nanopore DNA sequencing, Tunnelling currents DNA sequencing, Sequencing by hybridization, Sequencing with mass spectrometry, Transmission electron microscopy DNA sequencing, RNAP (RNA Polymerase) sequencing or Single-molecule real-time sequencing.

IX Applications of PINSswift

IX.i Research and Development Applications of PINSswift

Use of PINSswift to isolate or enrich target DNA molecule in mixed sample of DNA molecules extracted from samples collected from the environment, or from clinical samples provides direct access to the genome, or parts thereof, that cannot be analysed by other methods because of the sample complexity. PINSswift is particularly useful for isolating or enriching DNA molecules involved in hereditary diseases, cancer, and infectious diseases.

Multiplex PINSswift is particularly useful for simultaneous isolation or enrichment of more than one target DNA molecule from samples comprising several target DNA molecules, such as a sample to be analysed for the DNA sequence of more than one virus, more than one hereditary disease or more than one cancer related gene.

PINSswift is also particularly useful for obtaining target DNA molecule sequence information from samples where only a small part of the sequence is known prior to enrichment, since the technique only requires a small part of the target DNA molecule sequence to be known in order to perform the detection step and furthermore takes advantage of high fidelity of polymerases (like Phi polymerase) in the MDA amplification to generate large amplified DNA molecules of up to 100,000 bp.

IX.ii Sample Preparation for Sequencing

When performing sequencing of large DNA molecules such as genomes, the sequence information obtained will often contain gaps where the sequenced molecules do not overlap or cannot be assembled. PINSswift is particularly useful for gap closing of DNA sequences, as PINSswift will retrieve up to 100,000 bp of sequence surrounding the small detection area and can therefore be designed to cover the unknown gap region.

PINSswift is also particularly useful when sequencing samples containing more than one variant of a target DNA molecule sequence such as chromosomal DNA containing two alleles of a gene. In this case, droplets containing each detection sequence are collected in separate compartments to ensure that only one copy of the sequence is present. The droplet may subsequently be barcoded separately to enable the separate sequencing of each variant of the target DNA molecule sequence.

IX.iii Diagnostic Applications of PINSswift

PINSswift may be used to analyse target DNA molecule in samples derived from multicellular organisms, such as a biopsy or a sample of body fluid or faeces obtained from a subject (e.g. human or animal subject), for the diagnosis or monitoring the progress of a medical indication or disease.

Diagnosis of a wide range of medical indications in a subject such as a disease caused by an infectious agent (e.g. micro-organism or virus) can be assisted by the isolation or enrichment and detection of a target DNA or RNA molecule that is derived from the genome of the infectious agent by PINSswift or Multiplex PINSswift, where the target DNA molecule is detected in a sample of mixed DNA molecules derived from a biopsy or sample of body fluid obtained from a patient.

Use of PINSswift in target DNA molecule isolation provides the additional feature, that additional diagnostic features of the disease can be determined. For example, where the genome of the infectious agent comprises resistance genes that confer resistance to certain therapeutic agents, enrichment of a resistance gene may also retrieve the region surrounding the resistance gene and may provide information about the specific infectious agent carrying the resistance.

PINSswift may be applied to diagnostics such as detection of presence of an infectious agent such as a prokaryotic organism and antibiotic resistance. Such cases can be the presence of methicillin resistance (MR) in Staphylococcus aureus (SA). The combination of (MRSA) is a well-known problem in hospitals and similar facilities, whereas MR may not cause comparable problems if it is not present in SA. PINSswift can be used for detection of co-existence of MR and SA if a method such as duplex detection is applied. Such duplex detection can be a dual-reporter detection system, where one detection system is used to monitor the presence of one event such as MR whereas another detection system is used to monitor the presence of another event, such as presence of SA within the same droplet. When both MR and SA are present in the same droplet, the two loci are likely to be localized on the same DNA fragment. Moreover, PINSswift can be applied to selectively retrieve additional DNA sequences from the host genome based on the presence of genes such as MR or SA. Thus, it can be used to provide additional sequence information from the genome of the infectious organism, which is of importance for bacterial typing.

PINSswift may also be used to assist diagnosis of a disease caused by, or originating from the presence of a viral agent in a subject. Using multiplex PINSswift, the presence or absence of viral DNA at a known integration site can be determined by tracking the co-enrichment of the viral DNA and integration site DNA sequence.

PINSswift may be applied to multiple genes within a single genome or within multiple genomes, which may be detected by any suitable molecular detection method. If required, a series of multiplex PCR reactions can be carried out and differentiated using specific dyes for each reaction. This can be done by introduction of detection systems such as probes such as Taqman probes, Scorpion probes, Molecular Beacon probes or similar. Moreover, PINSswift can also be applied to a series of genes which are not necessarily differentiated at the point of detection. Differentiation can be applied after sequence retrieval, using such methods as bar-coded PCR or similar.

X PINSswift and Bias in Amplification

PINSswift is based on specifically selecting samples where amplification of a desired DNA region from a complex, mixed DNA sample has occurred. Although Phi29 polymerase based amplification (MDA) has been described repeatedly as the most reliable genome amplification currently available, it is known to introduce significant bias. Pan et al. [18] states in general terms that a highly specific whole genome amplification (WGA) of complex DNA pools which avoids amplification bias remains a challenge. Moreover, similar observations are seen with alternative amplification methods such as DOP-PCR and random priming PCR. These two amplification methods are described as being much less efficient at reproducing the locus representation [19], resulting in even more biased amplification products. While bias is seemingly unavoidable, regardless of the amount of reaction template [20] present, the amount of template independent product (TIP) or bias introduced during amplification is seemingly correlated negatively to the amount of DNA template in the reaction and has in some studies been documented to represent 70-75% of the total yield [18]. Whole genome amplification is applied to amplify DNA in the PINSswift process and it would therefore be expected that these general challenges relating to bias in genome amplifications would also apply to PINSswift. As a procedure including WGA it would thus be expected that significant bias against the target DNA molecule should be observed. Hence a procedure such as PINSswift employing WGA would not have been considered as a method capable of enriching for a specific region of DNA in a mixed sample.

Surprisingly, the challenge of TIP/bias is not seen when applying the PINSswift technique, because the step of general amplification (e.g. MDA) is performed in at least $1.2 \times 10^6$ droplets per 5 µL MDA reaction mixture, each droplet having a volume of 5 pL or less; where the total amount of DNA molecule amplified is less than 300 fg (more commonly ≤50 fg). Under these conditions, amplification of the DNA molecules (normally 1 target DNA molecule and ≤2 non-target molecules in each droplet) is reagent-limited due to the pL volume of MDA reagents in each droplet. As a result, the target DNA molecule is effectively amplified while non-target DNA molecules, that might otherwise be preferentially amplified by Phi29 polymerase, are not over-represented in the final product. As stated above, performing general amplification in these droplets also serves to eliminate amplification of contaminating DNA molecules (see Example 5). The successful implementation of the PINSswift method was not expected because the amplification of the target DNA molecules in the general amplification step requires a combination of pL reaction volumes and a template of as low as one to two DNA molecules. Such conditions for general amplification have never previously been attempted, not least because ng amounts of template are recommended for Phi polymerase amplification, and because effective enzyme concentrations are known to fall dramatically in small volume reactions due to surface adsorption at the oil-water interface (see Example 6).

The minimal negative TIP/bias observed in the PINSswift system is significantly lower than the overall gain obtained from the amplification process and the net result is therefore a substantial enrichment of the target DNA molecule.

EXAMPLES

Example 1. Enrichment of Two Regions of DNA from *Escherichia coli* Mixed into Human Genomic DNA and Subsequent Sequencing The procedure employed is shown schematically in FIG. 5.

DNA Sample and Detection Reagents

1 µL of a DNA sample containing 0.2 pg/µL of chromosomal *Escherichia coli* DNA and 1 pg/µL of HeLa human chromosomal DNA was mixed with standard PCR reagents to a total volume of 10 µL. One region (*E. coli*—amplicon1) was targeted by primers "MB8 Fw1 tm60" and "MB8 Rev1 tm60" annealing to *Escherichia coli* AspartokinaseI (thrA) together with molecular beacon probe "MB 8.7" annealing to the region between the two PCR primers. The second region (*E. coli*—amplicon2) was targeted by primers "ThrB-fw" and "ThrB-Re" annealing to *Escherichia coli* Homoserine kinase (thrB) together with Beacon-ThrB annealing to the DNA between the two primers.

Preparation of Droplets

5 µL PCR reaction+50 µL droplet oil (4% v/v ABIL EM90, 0.05% v/v Triton X100, 96% v/v Mineral oil [light oil for molecular biology; Sigma-Aldrich; #M5904]) was mixed on a vortex mixer generating approximately 2 million water-in-oil droplets of different sizes with an average volume of approximately 2.5 pL. Assuming an average fragment length of 50 kilobases, each droplet contains on average $1.8 \times 10^{-3}$ *Escherichia coli* fragments hereof approximately $1.7 \times 10^{-5}$ target fragments and $9.1 \times 10^{-3}$ human non-target fragments.

PCR

Emulsion PCR was performed with the following cycling conditions: 95° C. 2 min, 3×(95° C. 3 seconds, 56° C. 15 second), 25° C. 30 seconds.

Detection and Selection

The sample was transferred to a microfluidic chip with a sorting channel diameter of 100 µm using a syringe pump and transported into a t-junction sorting zone on the chip. The droplets were visualized using a camera and bright fluorescent droplets (positive droplets) were physically sorted into one channel while non-fluorescent or weakly fluorescent droplets were discarded and left unsorted and were subsequently discarded. When all droplets were sorted to either gate, the positive droplets (a total of 31) followed by an oil phase were removed from the chip using vacuum from a syringe pump followed by gravity flow and transferred to a 200 µL tube. The total amount of the DNA molecules in the detected droplets, following coalescence, is estimated to be 1.7 fg, assuming that the average size of a detected target DNA molecule is 50,000 base pairs.

General Amplification

10 µL of 10 mM Tris-HCl, pH 8 was added to the oil containing the sorted positive droplets. The droplets were coalesced by adding 40 µL perfluorooctan-1-ol, vortexing and centrifugation. The 10 µL water phase was transferred to a new tube containing reagents for MDA amplification, including Phi29 polymerase, dNTPs, random hexameric primers and suitable salts to reach a total volume of 20 µL. 50 µL oil (4% v/v ABIL EM90, 0.05% v/v Triton X100, 96% v/v Mineral oil [light oil for molecular biology; Sigma-Aldrich; #M5904]) was added and the two phases were mixed on a vortex mixer generating approximately 2 million water-in-oil droplets of different sizes with an average volume of approximately 5 pL. After two hours, the emulsion was broken by adding 40 µperfluorooctan-1-ol, vortexing and centrifugation, the water phase was transferred to a new tube and the Phi polymerase amplification process was repeated, and the emulsion was coalesced. The final water phase contained 370 ng/µL total DNA in 20 µL. The number of target DNA molecules was quantified using qPCR with primers annealing to a region adjacent to the primer pair used for detection (primers MB10.1fw and MB10.1rev).

Results

After enrichment as described above, the final sample contained $1.1 \times 10^{10}$ target copies per µL as quantified using qPCR as described above or 30000 targets per pg. This corresponds to an enrichment of approximately 1090 fold (calculated on a targets/pg total DNA basis). The sample was sequenced using Sanger sequencing and next generation sequencing (Illumina 150 bp paired-end sequencing) and both the expected *Escherichia coli* sequence were confirmed.

Example 2—Identifying a Point Mutation in Mixed Human DNA

The procedure employed is shown schematically in FIG. 5.

DNA Sample and Detection Reagents

Purified human DNA containing a point mutation at codon 12 (sequence GAT) in gene Kras (JX512447) was mixed 1:100 with a corresponding sample without the mutation in codon 12 (sequence GGT) (mutation frequency 1%). 1 µL of a DNA sample containing 330 ng of the mixed chromosomal DNA was mixed with standard PCR reagents to a total volume of 20 µL. Primers Kras-cdn12-fw (TAGTGTATTAACCTTATGTG—SEQ ID No: 19) and Kras-cdn12-re (TTACCTCTATTGTTGGAT—SEQ ID No: 20) annealing to Kras were used along with Taqman probe taqMan-Kras-cdn12 annealing to the region between the two PCR primers at the site of the mutation.

Preparation of Droplets

20 µL PCR reaction+60 µL droplet oil (4% v/v ABIL EM90, 0.05% v/v Triton X100, 96% v/v Mineral oil [light oil for molecular biology; Sigma-Aldrich; #M5904]) was mixed on a vortex mixer generating approximately 8 million water-in-oil droplets of different sizes with an average volume of approximately 2.5 pL. Assuming an average fragment length of 50 kilobases, each droplet contains in average 760 fragments hereof approximately $1.2 \times 10^{-4}$ target fragments corresponding to 1000 positive droplets in total.

PCR

Emulsion PCR was performed with the following cycling conditions: 95° C. 2 min, 3×(95° C. 5 seconds, 56° C. 15 second, 72° C. 15 seconds), 25° C. 30 seconds.

Detection and Selection

The sample was transferred to a microfluidic chip with a sorting channel diameter of 105 µm using a syringe pump and transported into an x-junction sorting zone on the chip. The droplets were visualized using a camera and bright fluorescent droplets (positive droplets) were physically sorted into one channel while non-fluorescent or weakly fluorescent droplets were sorted into the other channel. When all droplets were sorted to either gate, the positive droplets (a total of 950) followed by an oil phase were removed from the chip using vacuum from a syringe pump and transferred to a 200 µL tube. The total amount of the DNA molecules in the selected positive droplets is estimated to be 50 fg, assuming that the average size of a detected target DNA molecule is 50,000 base pairs.

General Amplification

10 µL of 10 mM Tris-HCl, pH 8 was added to the oil containing the sorted positive droplets. The droplets were broken by adding 200 µL mineral oil, vortexing and centrifugation. The 10 µL water phase was transferred to a new tube containing reagents for MDA amplification, including Phi29 polymerase, dNTPs, random hexameric primers, dithiothreitol (DTT) and suitable salts to reach a total volume of 20 µL. 60 µL droplet oil (4% v/v ABIL EM90, 0.05% v/v Triton X100, 96% v/v Mineral oil [light oil for molecular biology from www.sigmaaldrich.com, product M5904]) was added and the two phases were mixed on a vortex mixer generating approximately 4 million water-in-oil droplets of different sizes with an average volume of approximately 5 pL. After two hours at 30° C., the emulsion was broken by adding 120 µL mineral oil, vortexing and centrifugation, the water phase was transferred to a new tube and the emulsion was broken. The final water phase contained 0.098 ng/µL total DNA in 20 µL.

10 µL of the above enriched DNA sample was amplified using Phi29 polymerase in a total of 20 µL as described above. The resulting enriched sample contained 350 ng/µL total DNA (sample A).

10 pg of the first enriched sample (before the second round of Phi29 polymerase amplification) was subjected to a second round of enrichment by performing emulsion PCR, selecting and sorting positive droplets. Approximately 400 droplets were selected and sorted as described above and the sorted droplets were further amplified resulting in a sample of 412 ng/µL total DNA in 20 µL (B-sample).

The number of target DNA molecules in samples A and B were quantified using qPCR with primers annealing to a region adjacent to the primer pair used for detection.

Results

After enrichment as described above, the final Sample A contained $1.7 \times 10^7$ target copies per µL as quantified using qPCR as described above or 40 targets per pg. This corresponds to an enrichment of 13000 fold (calculated on a targets/pg total DNA basis).

The final Sample B contained $1.2 \times 10^{10}$ target copies per µL as quantified using qPCR as described above or 28000 targets per pg. This corresponds to an enrichment of 70 fold from Sample A and 910,000 fold from the initial sample (calculated on a targets/pg total DNA basis).

The sample was sequenced using Sanger sequencing and next generation sequencing (Illumina 150 bp paired-end sequencing) and the expected sequence including the point mutation was confirmed.

Example 3. Identification of the Sequence and Integration Point of a Virus Integrated into Human DNA from 50 pg of Total DNA The procedure employed is shown schematically in FIG. 7.

DNA Sample and Detection Reagents

1 µL of a DNA sample containing 50 pg/µL of HeLa human chromosomal DNA containing integrated HPV18 virus in 20 µL was mixed with standard PCR reagents to a total volume of 10 µL. Primers "HPV18 104 fw1" and "HPV18 105 rev1" annealing to HPV18 were used along with molecular beacon probe "HPV18 106p" annealing to the region between the two PCR primers. dUTP was added instead of dNTP to enable the subsequent removal of PCR product from the reaction.

Preparation of Droplets

10 µL PCR reaction+30 µL mineral oil droplet oil (4% v/v ABIL EM90, 0.05% v/v Triton X100, 96% v/v Mineral oil [light oil for molecular biology from www.sigmaaldrich.com, product M5904]) was mixed in a microfluidic chip for droplet generation generating approximately 200,000 water-in-oil mono disperse droplets of with an average volume of approximately 50 pL. Assuming an average fragment length of 50 kilobases and four copies of HPV18 per genome, each droplet contains on average 4.6 DNA fragments hereof approximately $3.0 \times 10^{-4}$ target fragments.

PCR

Emulsion PCR was performed with the following cycling conditions: 95° C. 2 min, 3×(95° C. 5 seconds, 56° C. 15 second, 72° C. 15 seconds), 25° C. 30 seconds.

Detection and Selection

The sample was transferred to a microfluidic chip with a channel diameter of 100 µm using a syringe pump and transported into a t-junction sorting zone on the chip. The droplets were visualized using a camera and bright fluorescent droplets (positive droplets) were physically sorted into one channel while non-fluorescent or weakly fluorescent droplets were sorted into the other channel. When all droplets were sorted to either gate, the positive droplets (a total of 57) followed by an oil phase were removed from the chip using vacuum from a syringe pump and transferred to a 200 µL tube. The total amount of the DNA molecules in the selected positive droplets is estimated to be 14.2 fg, assuming that the average size of a detected target DNA molecule is 50,000 base pairs.

General Amplification

10 µL reagents including UDG (uracil-DNA N-glycosylase) and buffers for removal of dUTP containing PCR products was added to the oil containing the sorted positive droplets. The droplets were coalesced by adding 200 µL mineral oil, vortexing and centrifugation. The 10 µL water phase was transferred to a new tube and incubated for 10 minutes at 37° C. followed by 1 minute at 95° C. for inactivation of UDG. Reagents for MDA amplification, including Phi29 polymerase, dNTPs, random hexameric primers and suitable salts were added to reach a total volume of 20 µL. 60 µL mineral oil was added and the two phases were mixed on a vortex mixer generating approximately 4 million water-in-oil droplets of different sizes with an average volume of approximately 5 pL. During incubation at 30° C., the droplets gradually fused resulting in an increased droplet size after the total of 4 hours incubation. The final water phase contained 275 ng/µL total DNA in 20 µL. The number of target DNA molecules was quantified using qPCR with primers annealing to a region adjacent to the primer pair used for detection (primers: HPV5901f (GTT-TAGTGTGGGCCTGTGC) and HPV5994r (GGCATGG-GAACTTTCAGTGT).

Results

After enrichment as described above, the final sample contained $1.5 \times 10^9$ target copies per µL as quantified using qPCR as described above or 5500 targets per pg. This corresponds to an enrichment of approximately 1100 fold (calculated on a targets/pg total DNA basis). The sample was sequenced using Sanger sequencing and next generation sequencing (Illumina 150 bp paired-end sequencing) and the sequences of the regions of four integrated copies of HPV18 including integration sites were determined.

Example 4. General Amplification of a DNA Target in Droplets Eliminates Amplification of Contaminating DNA All Phi29 polymerase amplification reaction mixtures were prepared in 25 µL volume using the RepliG single cell kit from Qiagen according to the manufacturer's recommendations. DNA purified from E. coli was used as template for the reactions. Duplicate samples were prepared, where the amplification reaction in one sample was allowed to proceed in the 25 µL volume (standard conditions); while the duplicate samples was first converted to droplets and then the reaction was allowed to proceed. When the reaction was performed in droplets, 50 µL of mineral oil droplet oil (4% v/v ABIL EM90, 0.05% v/v Triton X100, 96% v/v Mineral oil [light oil for molecular biology from www.sigmaaldrich.com, product M5904]) was added and vortexed for 1 minute generating approximately 5 million water-in-oil droplets of different sizes with an average volume of approximately 5 pL. The reactions were incubated for 16 hours at 30° C. The emulsion was then coalesced by adding 50 µL perfluorooctan-1-ol, vortexing and centrifugation and the 20 µL water phase was transferred to a new tube. 2 µL of each reaction was loaded onto a 0.7% agarose gel. The following amplification reactions were performed: 1) 1 ng E. coli DNA template, no droplets, 2) No DNA template, no droplets, 3) 1 ng E. coli DNA template, reaction in droplets, 4) No DNA template, reaction in droplets, 5) 1 ng E. coli DNA template, no droplets, no Phi29 polymerase.

Results

FIG. 8 shows an agarose gel of the size separated amplification products of the Phi29 polymerase amplifications. Significant amounts of amplified DNA can be seen in lanes 1-3 corresponding to an efficient amplification. As the reaction in lane 3 does not contain template DNA, the amplified DNA is likely to come from contaminating DNA in the reaction. When the non-template reaction was performed in droplets, no amplified DNA is visible on the gel (lane 4).

To investigate whether the amplified DNA from the Phi29 polymerase amplification reactions contains target DNA molecules (E. coli), quantitative PCR was performed on the amplified samples using E. coli specific primers C-Thr 1325f and C-Thr 1485r and the following cycle conditions: 94° C., 15 sec/60.5° C., 15 sec/72° C., 15 sec.

As can be seen from FIG. 9, only the Phi29 polymerase reactions comprising E. coli DNA template (1 and 3) produced specific product using the E. coli primer set. This was the case for both the droplet and the non-droplet reaction. The Phi polymerase reaction without template and without droplets (FIG. 8, Lane 2) did not result in any specific qPCR amplification although large amounts of DNA were present (FIG. 9, 2) suggesting that the DNA generated by the Phi29 polymerase reaction was amplified from contaminating non-E. coli DNA.

The analysis further demonstrates that on average 0.2 fg template per droplet is sufficient for Phi29 polymerase mediated general amplification, when the reaction is performed in droplets having an average volume of 5 pL, as is the case for sample 3 comprising E. coli template.

Example 5. Enrichment and Sequencing of the Human Dusp3 Gene

The following experiment was performed to demonstrate the detection, enrichment and sequencing of a target DNA molecule in a sample of mixed DNA molecules, where the frequency of the target DNA molecule in the sample of mixed DNA molecules was between $10^{-5}$ and $10^{-7}$ (calculated as base pairs of target sequence divided by base pairs of total DNA in the sample) and the target DNA molecule comprised from between 10,000 to 100,000 nucleic acid base pairs.

The experiment was performed according to the method of the invention, where the sample of mixed DNA molecules was detected by PCR in droplets, where the frequency of target DNA molecules was between $10^{-4}$ to $10^{-5}$ target DNA molecules per droplet. Approximately 100 fg DNA was recovered from positive droplets comprising the target DNA molecule, and a sample thereof was subsequently generally amplified. Amplification reaction was performed in droplets having a size of about 5 pL.

DNA Sample and Detection Reagents

1 µL of a DNA sample containing 1 ng/µL of human chromosomal DNA (Jurkat) was mixed with standard PCR reagents to a total volume of 20 µL. Primers "Dusp3 fw3" [5'-AGATGGTTTTGCCCGCTTT—SEQ ID No. 21] and "Dusp3 rev3" [5'-TGCCACTTAGCAGAAGCAAC—SEQ ID No. 22] annealing to the human DUSP3 gene (GenBank accession number NM_004090.3) were used along with Taqman probe "Dusp3 tp3-2 FAM" [FAM-CCACCT-CATATGTGTGTGCTGCC-BHQ1—SEQ ID No. 23] annealing to the region between the two PCR primers. dUTP was added instead of dNTP to enable the subsequent removal of PCR product from the reaction.

Preparation of Droplets

20 µL PCR reaction and 30 µL mineral oil droplet oil (4% v/v ABIL EM90, 0.05% v/v Triton X100, 96% v/v Mineral oil [light oil for molecular biology; Sigma-Aldrich; #M5904]) were mixed in a microfluidic chip for droplet generation and approximately 6,500,000 water-in-oil mono disperse droplets were generated, where the average droplet volume was approximately 3 pL. Assuming an average fragment length of 50 kilobases and one copy of the DUSP3 gene per genome, each droplet contains on average 2.6 DNA fragments hereof approximately $4.2 \times 10^{-5}$ target fragments.

PCR

Emulsion PCR was performed with the following cycling conditions: 94° C. 2 min, 40×(94° C. for 3 seconds, 60° C. for 30 seconds), 25° C. for 30 seconds.

Detection and Selection

The sample was transferred to a fluorescence activated cell sorter (Biorad S3e). Positive droplets were physically sorted into one gate while non-fluorescent or weakly fluorescent droplets were sorted into the waste collection. When all droplets were sorted to either gate, the positive droplets (a total of 592) were transferred to a 200 µL tube.

General Amplification

The sorted positive droplets were coalesced by removing excessive oil, adding 2×10 µL 1H, 1H, 2H, 2H, Perfluorooctanol, and mixing and centrifuging the mixture. A 3 µL sample (approximate 30 fg) of the water phase of the coalesced droplets was added to a 17 µL mix containing N6 hexamer primer, water, dNTP, 2.5 unit Phi29 polymerase. 20 µL 2% PicoSurf oil was added and the reactions were then vortexed for 2 minutes at 2600 rpm to generate water-in-oil droplets where the average droplet volume was approximately 5 pL. The droplets were incubated at 30° C. for 6 hours and then the enriched and amplified DNA in the coalesced droplets was analysed using qPCR and Tapestation (Agilent) measurements. According to these measurements, the 3 µL DNA sample, following enrichment and amplification, now contained 60,000 target molecules. Since the total DNA concentration was below 0.5 ng/µL, which is the lower limit of detection of the Tapestation, a second round of general amplification in droplets was therefore performed as above to increase the amount of total DNA.

Results

The result of the second amplification in droplets was as follows in Table 1:

TABLE 1

| Sample | Cq | copies/ul | ng/ul | copies/ng | Enrichment* |
|---|---|---|---|---|---|
| 2nd Phi 592 3 ul | 16.16 | 23187840 | 31 | 747995 | 2693 |

*Enrichment is relative to the original Jurkat DNA sample.

After enrichment as described above, the final sample contained $2.3 \times 10^7$ target copies per µL as quantified using qPCR. This corresponds to an enrichment of approximately 2700 fold (calculated on a targets/pg total DNA basis). The sample was sequenced using next generation sequencing (Illumina 150 bp paired-end sequencing). A 14.5 kb sequence contig [SEQ ID No. 24] covering the DUSP3 gene target region was generated from the NGS data.

Example 6. Enzyme Inactivation as a Result of Adsorption to the Water/Oil Interface Introduction This example shows the effect on droplet-based Phi29 polymerase amplification as a function of reduction in droplet size. It is expected that the Phi29 polymerase reaction will be inhibited in small droplets based on prior art where enzymes are described as being highly susceptible to adsorption to the interphase between water and droplet oil [11]. Moreover, it has been thoroughly described, that the increased surface to volume ratio causes an increased inhibition when performing enzymatic reactions in droplets [12].

Due to progressive inactivation of enzymes resulting from nonspecific adsorption at the oil-water interface, Phi29 polymerase amplification in small size droplets is expected to be inhibited. Nonetheless, droplets created in this experiment (in the femto-to-picoliter range and, thus, expected to result in inhibition) seemingly do not inhibit the Phi29 polymerase amplification, as DNA yield from different sizes of Phi29 polymerase droplets are close to identical (Table 3 Results from Droplet Phi).

Procedure

Two parallel 20 µl samples were prepared for Phi29 amplification as described in Example 5 where 3 ng Jurkat DNA template (Thermofisher Scientific) was added to each of the reactions. 40 μl 2% PicoSurf (Dolomite Microfluidics) was then added to the samples and both were vortexed at different velocities as described in the table below. "Hand-pulled on Eppendorf holder" is a method where a 1.5 mL Eppendorf-tube containing the reaction mixture is held at an angle of approx. 45 degrees and forced over the top of a 16-hole 1.5 mL tube holder, while applying moderate pressure to the tube ensuring an up/down movement in each of the holes (of the tube holder) when pulled rapidly and horizontally over the top to the holder. This procedure results in the Eppendorf tube moving up and down approx. 5 mm at a frequency of 27 vertical movements per second.

The procedure is repeated 5 times over a total period of 3 seconds.

TABLE 2

Sample parameters

| Sample A | Sample B |
|---|---|
| 20 μl Phi29-amplification mixture (3 ng) | 20 μl Phi29-amplification mixture (3 ng) |
| 40 μl PicoSurf (2%) | 40 μl PicoSurf (2%) |
| Vortex (1600 rpm)-60 sec | Hand-pulled on Eppendorf holder |

Template and Droplets

Average sizes of the resulting droplets were measured using microscope images and associated measuring software. Based on the average droplet sizes the total number of droplets was calculated from each sample. Based on an estimated template fragment size of 30 Kb, a template amount of 3 ng DNA will be equivalent to $9.3 \times 10^7$ fragments of DNA. Thus, the preparation of both samples A and B resulted in droplets where DNA was present (details in Table) in all created droplets.

The droplets generated for both samples were then incubated for 6 hours at 30° C. and the reactions were terminated by raising the temperature to 65° C. for 10 minutes. The content of the droplets was extracted by applying PicoBreak as described by the manufacturer. SSO Advance Supermix (BioRad) was used to quantify the target region (Dusp3) using RealTime PCR quantification (Ct). Total DNA after amplification was measured using a TapeStation (Agilent).

Results

A collection of results are presented in Table. Briefly, the data presented in the table shows that the average measured diameter correlated to the intensity of the vortex applied. Sample A, where the most gentle handling was applied resulted in an average droplet diameter of 45.7 μm whereas the hardest physical vortex (Sample B) resulted in droplets with an average diameter of 13.3 μm.

Upon Phi amplification and product extraction, DNA-quantification showed more than double quantities of amplified DNA from Sample A (28.5 ng/μl) compared to sample B (13.2 ng/μl). Regardless of the surplus of template in both samples (template is present in all droplets) an approximately two-fold lower level of total DNA was observed in the reaction performed in the smaller droplets. If inhibition had not occurred, comparable DNA amounts would be expected as the total reaction volumes of both samples are identical and template is present in all droplets. Ct values in the product from the two reactions were similar. Although this indicates that some inhibition may occur, significant amounts are still produced from the amplification in the smaller droplets and subsequent use in downstream sequencing is still possible.

The results obtained here suggest that droplet size (ranging from 1.2 to 50 pL) is of importance for amplification yields but that the Phi29 polymerase is relatively insensitive to the inhibition and that the inhibition effect does not prevent downstream use in sequencing.

TABLE 3

Results from Droplet Phi*

| | Avg diameter (μm) | Droplets per 20 μl | DNA fragments pr. droplet | Phi29 amplification prod (ng/μl) | Ct |
|---|---|---|---|---|---|
| Sample A | 45.7 | 4.01E+05 | 2.32E+02 | 28.5 | 27.29 |
| Sample B | 13.3 | 1.61E+07 | 5.79E+00 | 13.2 | 27.86 |

*The table shows data from amplification in droplets. The average diameter and the number of droplets is estimated based on microscopy, DNA fragments per droplet is based on Tapestation measurement of the DNA prior to droplet generation and the average droplet size, the Phi29 polymerase amplification product is determined based on Tapestation measurements.

```
                      Sequence listing

MB8 Fw1 tm60:
                                                   [SEQ ID No: 1]
GACGGTAGATTCGAGGTAATGC

MB8 Rev1 tm60:
                                                   [SEQ ID No: 2]
TATGGCCGGCGTATTAGAAG

MB10.1fw:
                                                   [SEQ ID No: 3]
TCAACAACCTCGCATCGG

MB10.1rev:
                                                   [SEQ ID No: 4]
GTGCTGGCTGCCTGTTTAC HPV18 104 fw1:
                                                   [SEQ ID No: 5]
CAGATCCTTATGGGGATTCC HPV18 105 rev1:
                                                   [SEQ ID No: 6]
GATTGAGGCACAGTGTCAC HPV18 106p:
                                                   [SEQ ID No: 7]
GGCATTTTTGGAATAGGGCAGG HPV5901f:
                                                   [SEQ ID No: 8]
GTTTAGTGTGGGCCTGTGC HPV5994r:
                                                   [SEQ ID No: 9]
GGCATGGGAACTTTCAGTGT ThrB-Fw:
                                                   [SEQ ID No: 10]
ACATTCAGTCTCAACAAC ThrB-Re:
                                                   [SEQ ID No: 11]
AATTTGCTTACCCAGTTC Beacon-ThrB:
                                                   [SEQ ID No: 12]
CGCGATCGTTCTGACGGCAGCTTATCGGATCGCG E. coli amplicon1 (ThrA)
                                                   [SEQ ID No: 13]
GACGGTAGATTCGAGGTAATGCCCCACTGCCAGCAGTTTTTCGACCG

GATCGATAACAGTAACGTTGTGACCGCGCGCTTCTAATACGCCGGCC

ATA
```

-continued

Sequence listing

E. coli amplicon2 (ThrB)
[SEQ ID No: 14]
ACATTCAGTCTCAACAACCTCGGACGCTTTGCCGATAAGCTGCCGTC

AGAACCACGGGAAAATATCGTTTATCAGTGCTGGGAGCGTTTTTGCC

AGGAACTGGGTAAGCAAATT

K-ras amplicon
[SEQ ID No: 15]
TAGTGTATTAACCTTATGTGTGACATGTTCTAATATAGTCACATTTT

CATTATTTTTATTATAAGGCCTGCTGAAAATGACTGAATATAAACTT

GTGGTAGTTGGAGCTGATGGCGTAGGCAAGAGTGCCTTGACGATACA

GCTAATTCAGAATCATTTTGTGGACGAATATGATCCAACAATAGAGG

TAA

HPV18 amplicon
[SEQ ID No: 16]
GATTGAGGCACAGTGTCACCCATAGTACCTGCCCTATTCCAAAAATG

CCTAGCAAAAAGCTGCTCACGCCGTAAGCAAAAAAACATGGAATCCC

CATAAGGATCTG

C-Thr 1325f:
[SEQ ID No: 17]
CCCGCGCCAATATCAACA

C-Thr 1485r:
[SEQ ID No: 18]
ACCGACGCCAATCACAAACA

REFERENCES

1. Tan, Y-C., et al., *Monodipersed microfluidic droplet generation by shear focusing microfluidic device.* Sensors and Actuators, 2006, B114: 350-356
2. Sharma, S., et al., *Droplet-based microfluidics.* Methods in Molecular Biology, 2013. 949: p. 207-30.
3. Hindson, B. J., et al., *High-throughput droplet digital PCR system for absolute quantitation of DNA copy number.* Anal Chem, 2011. 83(22): p. 8604-10.
4. Sambrook, J. and D. W. Russell, *Molecular Cloning a laboratory manual.* 2001: Cold Spring Harbor Laboratory Press.
5. Walter, N. G., *Single molecule tools: fluorescence based approaches, part A. Preface.* Methods in Enzymology, 2010. 472: p. xxi-xxii.
6. Kintses, B., et al., *Microfluidic droplets: new integrated workflows for biological experiments.* Current Opinion in Chemical Biology, 2010. 14(5): p. 548-55.
7. Rinke, C., et al., *Obtaining genomes from uncultivated environmental microorganisms using FACS-based single-cell genomics.* Nat. Protocols, 2014. 9(5): p. 1038-1048.
8. Agresti, J. J., et al., *Ultrahigh-throughput screening in drop-based microfluidics for directed evolution.* Proc Natl Acad Sci USA, 2010. 107(9): p. 4004-9.
9. Longo, M. C., M. S. Berninger, and J. L. Hartley, *Use of uracil DNA glycosylase to control carry-over contamination in polymerase chain reactions.* Gene, 1990. 93(1): p. 125-8.
10. Prodělalová, J., et al., *Isolation of genomic DNA using magnetic cobalt ferrite and silica particles.* Journal of Chromatography A, 2004. 1056(1-2): p. 43-48.
11. Pandit, K. R., et al., *Assessment of surfactants for efficient droplet PCR in mineral oil using the pendant drop technique.* Colloids Surf B Biointerfaces, 2015. 126: p. 489-95.
12. Liu, Y., S.-Y. Jung, and C. P. Collier, *Shear-Driven Redistribution of Surfactant Affects Enzyme Activity in Well-Mixed Femtoliter Droplets.* Analytical Chemistry, 2009. 81(12): p. 4922-4928.

The invention claimed is:

1. An in vitro method for enriching one or more target DNA molecule from a sample of mixed DNA molecules comprising the steps of:
   a) providing a liquid sample of mixed DNA molecules comprising one or more specific target DNA molecule and reagents for specific detection of at least one of said target DNA molecules,
   b) forming an emulsion of a multiple of liquid droplets from said liquid sample,
   c) specifically detecting droplets containing at least one of said target DNA molecules, wherein each droplet contains less than 0.5 of said one of more target DNA molecule on average,
   d) physically selecting droplets containing at least one of said target DNA molecules, and coalescing the selected droplets, and
   e) amplifying detected DNA molecules containing at least one of said target DNA molecules in the coalesced selected droplets from step d), where the detected DNA molecules containing at least one of said target DNA molecules are in a total amount of less than 300fg, wherein general amplification reagents are added to the coalesced selected droplets to form a general amplification reaction mixture, and wherein an emulsion of droplets are formed from the reaction mixture.

2. The method according to claim 1, wherein in step e) from at least $1.2 \times 10^6$ and up to a maximum of $1.2 \times 10^9$ droplets are formed for each 5 µl of the reaction mixture.

3. The method according to claim 1, wherein the total number of droplets in step b) is at least $5 \times 10^5$.

4. The method according to claim 1, wherein the reagents are PCR reagents and specific detection of said one or more target DNA molecule is performed by PCR.

5. The method according to claim 1, wherein said target DNA molecule comprises one or more unique consecutive sequence of at least 40 nucleotides.

6. The method according to claim 1, wherein the general amplification of DNA in step (e) is performed by Multiple Displacement Amplification.

7. The method according to claim 1, wherein the reagents for specific detection contain dUTP.

8. The method according to claim 7, wherein step (d) further comprises the step of inactivating, degrading or removing DNA produced for specific detection of said one or more target DNA molecule.

9. The method according to claim 8, wherein the step of inactivating is performed using uracil-DNA N-glycosylase.

10. The method according to claim 1, further comprising a step (f) of repeating steps (a) to (e), wherein the DNA molecules in said liquid sample of repeated step (a) are derived from amplifying products generated from the DNA molecules in the coalesced selected droplets in step (e).

11. The method according to claim 1, wherein each of the droplets formed in step b) have an average diameter from 2 to 20 µm.

12. The method according to claim 1, wherein the droplets formed in step b) contain on average at least $10^{-7}$ target DNA molecule per droplet.

13. The method according to claim 1, wherein each of said one of more target DNA molecule of step a) comprises 1,000 to $10^8$ nucleic acid base pairs.

14. The method according to claim 1, wherein the general amplification product generated in step e) comprises one of more amplified target DNA molecule, wherein each amplified target DNA molecule comprises 500 to 150,000 nucleic acid base pairs.

15. The method according to claim 1, wherein the target DNA molecule is derived from the genome of a cell.

16. The method according to claim 1, wherein in step (e) the droplets formed from the reaction mixture are 0.0042 pL to 1 nL water-in-oil droplets.

17. The method according to claim 1, wherein in step (e) the droplets formed from the reaction mixture are 1 pL to 1 nL water-in-oil droplets.

18. The method according to claim 1, wherein in step (c) each droplet contains less than 0.1 of said one of more target DNA molecule on average.

19. The method according to claim 12, wherein the droplets formed in step b) contain on average from $10^{-4}$ to $10^{-5}$ target DNA molecule per droplet.

20. The method according to claim 13, wherein each of said one of more target DNA molecule of step a) comprises 10,000 to 100,000 nucleic acid base pairs.

21. The method according to claim 1, wherein the general amplification of DNA in step (e) is performed by linker ligation PCR.

* * * * *

SEQUENCE LISTING

<160> NUMBER OF SEQ ID NOS: 24

<210> SEQ ID NO 1
<211> LENGTH: 22
<212> TYPE: DNA
<213> ORGANISM: Escherichia coli
<220> FEATURE:
<221> NAME/KEY: primer_bind
<222> LOCATION: (1)..(22)
<223> OTHER INFORMATION: MB8 Fw1 tm60 primer for E. coli thrA

<400> SEQUENCE: 1
gacggtagat tcgaggtaat gc                                            22

<210> SEQ ID NO 2
<211> LENGTH: 20
<212> TYPE: DNA
<213> ORGANISM: Escherichia coli
<220> FEATURE:
<221> NAME/KEY: primer_bind
<222> LOCATION: (1)..(20)
<223> OTHER INFORMATION: MB8 Rev1 tm60 primer for E. coli thrA

<400> SEQUENCE: 2
tatggccggc gtattagaag                                               20

```
<210> SEQ ID NO 3
<211> LENGTH: 18
<212> TYPE: DNA
<213> ORGANISM: Escherichia coli
<220> FEATURE:
<221> NAME/KEY: primer_bind
<222> LOCATION: (1)..(18)
<223> OTHER INFORMATION: MB10.1fw qPCR primer

<400> SEQUENCE: 3
tcaacaacct cgcatcgg                                                  18

<210> SEQ ID NO 4
<211> LENGTH: 19
<212> TYPE: DNA
<213> ORGANISM: Escherichia coli
<220> FEATURE:
<221> NAME/KEY: primer_bind
<222> LOCATION: (1)..(19)
<223> OTHER INFORMATION: MB10.1rev qPCR primer

<400> SEQUENCE: 4
gtgctggctg cctgtttac                                                 19

<210> SEQ ID NO 5
<211> LENGTH: 20
<212> TYPE: DNA
<213> ORGANISM: Human papillomavirus type 18
<220> FEATURE:
<221> NAME/KEY: primer_bind
<222> LOCATION: (1)..(20)
<223> OTHER INFORMATION: HPV18 104 fw1 primer for HPV

<400> SEQUENCE: 5
cagatcctta tggggattcc                                                20

<210> SEQ ID NO 6
<211> LENGTH: 19
<212> TYPE: DNA
<213> ORGANISM: Human papillomavirus type 18
<220> FEATURE:
<221> NAME/KEY: primer_bind
<222> LOCATION: (1)..(19)
<223> OTHER INFORMATION: HPV18 105 rev1 primer for HPV

<400> SEQUENCE: 6
gattgaggca cagtgtcac                                                 19

<210> SEQ ID NO 7
<211> LENGTH: 22
<212> TYPE: DNA
<213> ORGANISM: Human papillomavirus type 18
<220> FEATURE:
<221> NAME/KEY: primer_bind
<222> LOCATION: (1)..(22)
<223> OTHER INFORMATION: HPV18 106p primer

<400> SEQUENCE: 7 ggcattttg gaatagggca gg                                              22

<210> SEQ ID NO 8
<211> LENGTH: 19
<212> TYPE: DNA
<213> ORGANISM: Human papillomavirus type 18
<220> FEATURE:
<221> NAME/KEY: primer_bind
<222> LOCATION: (1)..(19)
<223> OTHER INFORMATION: HPV5901f primer
```

```
<400> SEQUENCE: 8
gtttagtgtg ggcctgtgc                                                19

<210> SEQ ID NO 9
<211> LENGTH: 20
<212> TYPE: DNA
<213> ORGANISM: Human papillomavirus type 18
<220> FEATURE:
<221> NAME/KEY: primer_bind
<222> LOCATION: (1)..(20)
<223> OTHER INFORMATION: HPV5994r primer

<400> SEQUENCE: 9
ggcatgggaa ctttcagtgt                                               20

<210> SEQ ID NO 10
<211> LENGTH: 18
<212> TYPE: DNA
<213> ORGANISM: Escherichia coli
<220> FEATURE:
<221> NAME/KEY: primer_bind
<222> LOCATION: (1)..(18)
<223> OTHER INFORMATION: ThrB-Fw primer for E. coli thrB

<400> SEQUENCE: 10
acattcagtc tcaacaac                                                 18

<210> SEQ ID NO 11
<211> LENGTH: 18
<212> TYPE: DNA
<213> ORGANISM: Escherichia coli
<220> FEATURE:
<221> NAME/KEY: primer_bind
<222> LOCATION: (1)..(18)
<223> OTHER INFORMATION: ThrB-Re primer for E. coli thrB

<400> SEQUENCE: 11
aatttgctta cccagttc                                                 18

<210> SEQ ID NO 12
<211> LENGTH: 34
<212> TYPE: DNA
<213> ORGANISM: Escherichia coli
<220> FEATURE:
<221> NAME/KEY: primer_bind
<222> LOCATION: (1)..(34)
<223> OTHER INFORMATION: Beacon-ThrB primer

<400> SEQUENCE: 12
cgcgatcgtt ctgacggcag cttatcggat cgcg                               34

<210> SEQ ID NO 13
<211> LENGTH: 97
<212> TYPE: DNA
<213> ORGANISM: Escherichia coli
<220> FEATURE:
<221> NAME/KEY: gene
<222> LOCATION: (1)..(97)
<223> OTHER INFORMATION: E. coli amplicon1 (ThrA)

<400> SEQUENCE: 13
gacggtagat tcgaggtaat gccccactgc cagcagttttt tcgaccggat cgataacagt  60
aacgttgtga ccgcgcgctt ctaatacgcc ggccata                            97

<210> SEQ ID NO 14
```

```
<211> LENGTH: 114
<212> TYPE: DNA
<213> ORGANISM: Escherichia coli
<220> FEATURE:
<221> NAME/KEY: gene
<222> LOCATION: (1)..(114)
<223> OTHER INFORMATION: E. coli amplicon2 (ThrB)

<400> SEQUENCE: 14
acattcagtc tcaacaacct cggacgcttt gccgataagc tgccgtcaga accacgggaa      60
aatatcgttt atcagtgctg ggagcgtttt tgccaggaac tgggtaagca aatt           114

<210> SEQ ID NO 15
<211> LENGTH: 191
<212> TYPE: DNA
<213> ORGANISM: Homo sapiens
<220> FEATURE:
<221> NAME/KEY: N_region
<222> LOCATION: (1)..(191)
<223> OTHER INFORMATION: K-ras amplicon

<400> SEQUENCE: 15
tagtgtatta accttatgtg tgacatgttc taatatagtc acattttcat tattttatt      60 ataaggcctg ctgaaaatga ctgaatataa acttgtggta gttggagctg atggcgtagg     120
caagagtgcc ttgacgatac agctaattca gaatcatttt gtggacgaat atgatccaac     180
aatagaggta a                                                          191

<210> SEQ ID NO 16
<211> LENGTH: 106
<212> TYPE: DNA
<213> ORGANISM: Human adenovirus type 18
<220> FEATURE:
<221> NAME/KEY: gene
<222> LOCATION: (1)..(106)
<223> OTHER INFORMATION: HPV18 amplicon

<400> SEQUENCE: 16
gattgaggca cagtgtcacc catagtacct gccctattcc aaaaatgcct agcaaaaagc     60
tgctcacgcc gtaagcaaaa aaacatggaa tccccataag gatctg                    106

<210> SEQ ID NO 17
<211> LENGTH: 18
<212> TYPE: DNA
<213> ORGANISM: Escherichia coli
<220> FEATURE:
<221> NAME/KEY: primer_bind
<222> LOCATION: (1)..(18)
<223> OTHER INFORMATION: C-Thr 1325f primer

<400> SEQUENCE: 17
cccgcgccaa tatcaaca                                                   18

<210> SEQ ID NO 18
<211> LENGTH: 20
<212> TYPE: DNA
<213> ORGANISM: Escherichia coli
<220> FEATURE:
<221> NAME/KEY: primer_bind
<222> LOCATION: (1)..(20)
<223> OTHER INFORMATION: C-Thr 1485r primer

<400> SEQUENCE: 18
accgacgcca atcacaaaca                                                 20
```

```
<210> SEQ ID NO 19
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Kras-cdn12-fw  primer

<400> SEQUENCE: 19
tagtgtatta accttatgtg                                              20

<210> SEQ ID NO 20
<211> LENGTH: 18
<212> TYPE: DNA
<213> ORGANISM: Homo sapiens
<220> FEATURE:
<221> NAME/KEY: primer_bind
<222> LOCATION: (1)..(18)
<223> OTHER INFORMATION: Kras-cdn12-re  primer

<400> SEQUENCE: 20
ttacctctat tgttggat                                                18

<210> SEQ ID NO 21
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Dusp3 fw3 primer

<400> SEQUENCE: 21
agatggtttt gcccgcttt                                               19

<210> SEQ ID NO 22
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Dusp3 rev3 primer

<400> SEQUENCE: 22
tgccacttag cagaagcaac                                              20

<210> SEQ ID NO 23
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Polynucleotide portion of Dusp3 tp3-2 FAM
      Taqman probe

<400> SEQUENCE: 23
ccacctcata tgtgtgtgct gcc                                          23

<210> SEQ ID NO 24
<211> LENGTH: 14528
<212> TYPE: DNA
<213> ORGANISM: Homo sapiens
```

<400> SEQUENCE: 24

```
gggggcgggg gcgcaggtag aggcgtgggg gagaaggatt cacacctgag gtgcaataag      60
gaaaggaagg ccagaggaat ctttcattga agacagattg tttgaggaca agcagctcct     120
gtgaagaggc tgcccagatc ctctggtatt ttaactgggc aatgaatcag catgccccac     180
ctgcagagcc tctgcaagtc ctttgccacc tgcctcaact tgcaagtcgc tgtgtccatc     240
tgcagccgac tgtcctttcc atcatccatc atccgacaca tgaatgcagc tgctctgaca     300
gttttacaag ccagacagaa gcccctcag gaagggccct ctctgatacc tgcttcctaa      360 gtcagttttcc ttcagggcag atgaaaacag ctgtggccat tgttgggggt gatctatctc    420
tcccagcaga gccggtagtg ttgtgagaag ctggccctcc gcgccacctc cccttgtcta     480
tgaccctcca gcctccttt cccttgctct ggaatgtgga ctgttaaccc tctcatgacc      540
agacgactgc cttcttgcaa tggacttggg agagagcagt tctgatgcct gggttccttg     600
agcaggtagg atggatgctt atagccccac ctgctgttgg gagcggctgg accgtctgca     660
ttaaacagag gcagtgggat tcatccctgg aacgcgtctg ccacctgctg gagacaaaag     720
gaggggtgac tgcaggatgg caagtctcag gactggacgt gatttccttt cctttccttt     780
ccttatttgg aagtgaagta atattaaaag gaaaagaag aatccagtgg acttgaacct      840
ctaaatgatc cacacccctc tgaatggctc agcgagaacc tgctgtgaca tcttctgctg     900
tttcatttaa tgttaagtca ttgacagctg tttatttta ctcagtccac aaacttgtca      960
ttgttcacag tattccctgg aattaaaccc ccagggtttt agctgattcc tattgtgagt    1020
agtttaggtt atttccaatt ttttttccta tttccagcag ggttgctatg aacatccttg    1080
tacggctgaa attttttttt tttctttttt tggcagattc tctctgtggc ccaggctgca    1140
gtgcagtggc acaatcttgg ctcactgcaa cctccacctc ctgggttcaa gcaattctcc    1200
tgcctcagcc tcccgagtag ctgggattac aggaatgcac caccacgccc ggccaatttt    1260 gtattttag tagagacggg ggtttctcca tgttactcag gctggtctcg aacttctgac      1320
ctcgggtgat ctgcccaact cggcctccca aggtgctggg gattagaggc atgagccaca    1380
atgcccggcc tcagagtaat ttttttaaatt aaaattttaa aatgtggata taattataaa    1440 tttaaaatata cttataagaa ataaaagccc gggcaacatg gtgaggccta gtctctacaa    1500
aaaatttaaa aattagctgg gcatggggtc gcacgcctgt ggtcttagct acttgggagg    1560
ctgaggtggg aggttcactt gaggttgagg tcgaggctgc agtgagccat acttgggcca    1620
ctgcactcca gcctggttga cagagtgaga ccccgtctca aaaataaaa ataaaaaaaa      1680 gaaaatgcag actccgtgta tccttatcc agtttcccac aacaataaca ccttgcgaaa      1740
ctataggaca atatcacaac taggatattg atattgacac aatttaccaa tcttacccac    1800
atctcccgtg gcttaaccctc tactgtgtgc gtgcacacgc attcacgtgt gtgtatactt    1860
agttctatgc aatcttgtca cgggtaaatt tggggatcca ccacagtcaa gataaagcac    1920
agctctgtga ccacaagtct ttctcctgtt gcccacctcc ttccctcctt ttccctccct    1980
cccacaacta acccctggca actactcatc taatctccat ttctgtcatt ttttttttca    2040
cttcaaaatt gttacataaa tgcgaccagg tgcggtggct cactcatgta atcccagcac    2100
tttgggaagc caaggcaggc agatcacttg aggtcaggag ttcgagacca gcctggccaa    2160
catggcgaaa ccctgtctct actaaaaata caaaaattag ctgggcatgg tggcacgcac    2220
ctgtaatccc agctatttgg gaagctaagg caagagaatc gcttgaactc aggaggcgga    2280
```

```
agttgcagtg agctgagatc gcgccactgt gctccagcct gggtgacaga gtgagactgt    2340
ctcaaaaaaa aaaaaaaggt tatataaatg gaatcaatta gtatgtagcc tttggggatt    2400 ttttttttcac tcagcattat ttccattatc caagttgtac atatcagtaa catgttcctt   2460
tttcttttct tttttttttt ttggctgagt agtattccac aaagtttaaa aaaacaaaac    2520
aaaactttag agttatttct ggaagtgaat gctgtgtctg agggagtgtg aagagtttgg    2580
tggtctgatg agggtattgc agggctgttt tccagaaaac tcagcccagt ccccgccctc    2640
acctgcaaaa tagaggctcc cataggtggt actttgatga ggctgccgta actaagtacc    2700
acaaattggg tggcataaac aacagaagtc gtctcacaga gctggaggtt aggagtgcaa    2760
gttcaagaca ttggcagagt tggttccttc gaggacagtg aggaaggcct tttacctgcc    2820
ttctgctggc tgctgacaag ctgtggcatt cactggcttg cagaagtgtc accccccaatc  2880 cctgccttca tcttcacatg gtgttctctc tgtgttcgaa ttttcccttt tttctaagga    2940
ggtcaggcat attagattag gcccagccta acgacctcat cttaacgagt tacatctgta   3000
atagccctat ttccaaataa ggtcacattc tcaggtactg tgacttagga cttcaatata    3060
tgcatttggg aggaatgcag ttcaacccat aaataagact gtcaacactg ggtttgggat    3120
gttgattttt tttttttttt tttttttttt ttttgagaca gagtctcgct ctgtcaccca    3180
ggcgggagtg cagtggtgtg atcttggctc atataacctc cacctcctgg gttcaagcag    3240
ttctcctgcc tcagcctccc gagtagctag gactacagac tcccgccacc acacccagct    3300 aattttttgca tttttttttgt ttgttttgta gagatggggt ttcgccatgt cggccaggct    3360
ggtcttgaac tcctgacatc aggtgttccc acaatcccat aaagtgctgg gattgcaggc    3420
gggagccacc gcacccagcc gatttttttta acattgaat ttaacagttg aaacttaatt    3480
tccagaaaag ctgctttttcc atgtgattat ttaccagctt ttgtttctgt cgagttgctt    3540
cttccgatgt tcactcgcca aacgtttaat aaagcaaggg ggacacgcac tccctctcca    3600
ggagctcgca taccatggaa gaaataattt ccgcatccaa acaactccac taccagatgg    3660
aaggtgatca atgccactga aaaaaaggtt cagatgcttt tttctaaaaa aaactttatt    3720
ttttttctgg agcactttta ggttcacagc aaaactgagt ggatggtaca gagatttctc    3780
atttatgtcc tgtgcccaca catgtacagc tgcccccgtt atcaacatcc cgccaccaga    3840
gtggtgcatt tgctatgatt gatgagccta catgacacat cattatcacc tgaagtccat    3900
ggtttacatc acagcactag tgttgtacat cctatggctt tggacaaatg tataatgaca    3960
tacatctacc attatagtat catacagatg ggcagtattt tcattgtcca aaaaaactat   4020
ctgctctgcc tattcatccc tccccgactt tccccaaccc ctggcaacca ctgatcttttt   4080 tactgtacct ttatttttgc cttttccagg atgtcatata gagttggaat atacccatac    4140
atagtctttt cagattggct tctttcagtt agtaatattc atttggggtt cctccatgtc    4200
ttttcatggc atgaacagct tatttttttt ttttagcact gagtaatact ccattcgtct    4260
tgatgtatca cggtttatct agtcacctac tgtcatctac tgaaggacat cttggttgct    4320
ttcaagctct ggcaattatt aatagaggtg gtataaacat tttgcacagg tttttttgttt    4380 tgttttgtct taagacggag tcttactctg tctcccaggc tggggtgcag tgccgtgatc    4440
tcagctcact gcaacctccg cctcctgggt tcaagtgatt ctcctggctc agcctcccga    4500
gtaggtggga ttacaggtga gcaccaccac acctggctaa ttttttgtatt tttagtagag    4560 aagggggtttc cccatgttgg ccagtatggt ctcaaactcc taacctcaag tgatctgccc    4620
acctcagcct cccaaagtgc tgggattaca ggcatgagcc accatgccca gctgtgtgca    4680
```

```
ggtttttata cgaacgttaa gttttcaaat catttgaata aataccaagg agcatgactg   4740
ctggattgtg caataaaagt atgtgtagtt ttgcaagaaa ctaaactgca aactgtcctc   4800
caaagtggct gtaccatttt gcattccca ctgaaacaaa gagttcctgt tgttccacat    4860
cctcaccaga tgcattttt caaaaggaca attttcttat gggccttcaa aggagagaac    4920
aatctctttc ccctggggag gatctgggat ccttatggta agatgtggca tttggaccag   4980
actttgaatg acaggccaaa tttgaaagt atattatgct cctttgactc cttgggatca    5040
tagaatcttt gatctggaag gactctcaaa ggtcatccgg tttcattctc tacttggttc   5100
tggaggaggc ccctatctct aattaatgga aactgaggat tctccttatt ggctgcattt   5160
taaaacagat tttgctccca cttgtaggtg gtaaaagga aatatctgga ttaggagggc    5220
aaacttctgc tttaggcag taccctgcat tgagggatgt ccaaatcacc ttgtctttat    5280
ttacacatcc atacacaatg gaatgctatg tagctgttaa gatgaagggg gtagaacaat   5340
aaaaacaata accataatat aagctaagca aaacaaacaa caaagcagag atatctctgt   5400
atatacacac gtatgcacat atgtgtgctt atatatgctt gacattttcc tttaaggata   5460
tgatgcttat ggggagacag attgaaggag caagtgactc acttttccgt ataagccttt   5520
tgcattgttt aagtgtatta ctatgtacat atagtattat ttttaatgaa aaatttttta   5580
aaaattatac ttaaaaactt ttacctgttt tatattttag tgctctgcct taagattttg   5640
tgtagaacca taaagattac attgtcagag tcttgacaaa taggaagcga gtccaattgc   5700
ttcatgtgat agagggaatg ggaacctcga gaggctttct ctgcccagac ttctgtctgg   5760
gaggaaaagg caactacttt ctctaaggtt ttttattcaa aggaacatag caccaatagt   5820
ggaatttaag gcatctgggg gaagggggata tgtttaggga ctgttcattt gcaggatcac   5880
tcaaatctca aaatgtcacc cagtcatcac gtgaggctac cttgagatga acaccctagt   5940
cccctgcttt cttagaagca caaacctta ctccttcatt caggaccatt atggccattc     6000
tacctaagaa tattcctacc agaacatttc tggtactgga aaggtgttca tcaatatcta   6060
ctgcataaac agtgccatca tggaacctat aactagctca gaacggctat gttttagatg   6120
attattttta aaaagttaga aatcgcaaat ataaaagcta agcccaaaca aaaaaagcta   6180
agcataaaaa cgtaaaagaa taccaactgt gataagaagg acaaaaaaac aataccttg    6240 taatgtaaga catttatttt ggctaaagtt ctggtgtttt aacactgatt tgtgatacaa   6300
cggacattaa acttccttt aaaaagaaaa aaacaatttg gtagctctcc cttttctgtc    6360
cagaaaaatt cactctttca taatcaaatt accctaaaat ttggtggcgt taagaggcaa   6420
caaaagttaa gcttccaacg aatctgttct ctcaaccgga aatgtcttct atttccaatc   6480
aggataaaac cttgacttac ttgcaaggac tatcacggtt agcccttcag tgattcctga   6540
caccagttct gtgaaaaaga aaatttcctg cgagaaaagc tcatgtcttc atattgaaga   6600
tcagtacttt ttttttttc ctttaaaaca gtagcatctt aacttgtggc acaaaaggca   6660
ccaacattcc ctttccaaac catccatcac catgggtgga aggcagcgcc acctgctgcc   6720
catcatatta tggctcacat acccataatt tccttgcggt gctgaattcc aagtggggat   6780
tattagagac ccctcagagc caaaggggga ccttagaggt cttctagatg agtcccctca   6840
tttgtaggtg gtggtttctg gataactcag agtggcaggg acacagacga gcctgtggaa   6900
aggtatactg ctttaagatt gagaagaaaa ccatttggcg ctctaatttt gcctggatgg   6960
tgctctgtca gtcaaagaaa gggaacaggt ctggggaggg ggtaagggca ccctgagttc   7020
```

```
ctgttccatc acttcccagg cagtagaagg ctgtccagga acagctccca tccgcagctg    7080
ggcatgtgtt ggctcttaca caagagactt taattttact tgaagaacta agagctaaat    7140
cttgttaagt aaatacgggg tttcaggggt gaaggactat caagaaatcc caagttatca    7200
gcataaaagt agtcccaaag taaaggcagt aattctccca atggcctttt ctccctcatg    7260
cccccacaga gactttcgag aggtcctagt tagccagcca caccaacctg ctgtgttcgc    7320
gtaagtagct gtgcctgtcc catggggtga ccactgcctg gtcatgggag gggagcccca    7380
gccccagctc cctagccttt tccaggagca gagcagaaag ctctacttcg gggtgctaca    7440
tcccacctgg agaaagagct gcacattcta gcctatgagg gacccaccct tttcacttgc    7500
ttctccgggg ctggattgag ggtaagtgca gtacacctgg gatcccagg gagcccctt    7560 cttgagaaag agtatcgtat gaaagaatcc agcttcaggg agcagcaaac ccaaaatctt    7620
gcccagctcc accttatgga gctggacaac cctgggggcc aggcccttaa tcattctgaa    7680
cctcagttcc ttttttttaa aaaaggtcac aatacaagaa caagctctac taactttaca    7740
gggttactgt gaggctcaag ttagattaag ttggaaggct acctagaagc tgtgcagtga    7800
ggtacccagt ttagaggatg gccatttcac ttaggtgggt ttatctggac accttttttca    7860 ctatctggag aagaagacac atactggttg ttcagggctg ctgtggtcac agagaaaagc    7920
ggacagcaaa tgaccaggct gggcagggct gcttctgtgt gatcagagac cttcacagcc    7980
gggagtgagg ccttacgcca cacctgcctc tccgtgtccc agccaggagc tcctggccaa    8040
ctctgaaaaa ggcacattcc ctaccttggc atattaacac tgcctgaatt taaatgtaaa    8100
actgagttgt aaatagtcaa caaaagtccc tgatatttct ttcgttttag gtaagactcc    8160
ttcacaaggc cttgcgagtg atcctaccat gaattcagtc ttctgggagc gtgacacacc    8220
caccagaaca atgccctata tatatttggt gctcaaaaag tgtttaattt cttaaacttt    8280
tatcagacac ctatgtgcaa ggtgctgggg gcatggctga ggaccttctc tttgcccaga    8340
gtgaccctga agataaatag catcacaatc actttccata ataacaataa cgtaaaatcc    8400
taacaagact gtatttaaaa caaaactctt atattctggc aaatgtgcat acacatgtga    8460
gggctggtgc attccaatat catccttaga aagtcttttg aaaggtttat cgtgtttggg    8520 ttttttttgct ctaccaccaa taaaggatcc atttggacac tccaccatgt ctcatgtctg    8580
cctggctgag tcacttcagg gatcccgtgc tggcaccaga gagctgtaag agccacctgc    8640
aatgggcagg gtgtgtgcct gggaccttt acttccctgc ttgtcttctg gccgcgtttc    8700
tgagaggcac gcccccaca cacatccatg cacacacgct gtaattggcc aacttcctcc    8760
ttctgttctt ggaatagcaa ccgagacaaa aagcagttag cacgagtggc ttgggcttgc    8820
caacactaca attcaggaca aaaccccttgt aattctccaa atggtggggt ttttaaatag    8880
gttggacttc aactccctgt tttctaaaaa agaaaaaaaa aagcatgccc aaggcatcac    8940
tcttctcaaa aacgaagtga ctgagataag atcgaaggga aatattccag agcagcagat    9000
tctgaactca aggcttccaa agattcacat tttgaaaact ctatggattt aggagggttc    9060
tccaggtttg cccacaaggc ctctttgtgt agggaccatt catcctaagg aaatcattca    9120
aatgcagcct tgctgtggga atctccatcc actaataact gacggacacc cccaccccag    9180
cttcggacct caagacgtga gagggttgcc tatgcacagg gtgtggaagg ctgtggggac    9240
agtgcggggc acagacgtgg tgggagagt ggcctgcatt tgcatagttc ctttactagg    9300
gctcaaggtg ttgaggtcca cactcaagag aggattcggg agttgggaa gggaggtcat    9360 gagggacctc tgtgagcatc ttaggcctta cacttccaca cacctcctgc cgtgggccat    9420
```

```
cgggaagcat gcaggccaca ggccttcccc ctctgagccc ccatctcagg gaaaagacat    9480
cataagttac agaaacagga caactgggga gcaaggacgc ccccttggc aagcttcttt     9540 atgtgctccc cagggtgggg aaagtggccc aggactgtgt tgggacacac ttgtagacaa    9600
gtgccttgtg atgctgggag cagggtacag tgtgtttcct aaacatggca gctcgggaca    9660
cctttgccca cggcctcccc cacggacctc tcgagcagag gcggtggggg tgccctaggg    9720
tttcaacttc ccctccttgg ctagtctgtc attgagctgg cagagctggg ccaggaagcc    9780
atcgttgggg ccgatctcac ggttctgcct cacgatgctc agggcagact tgacgtccat    9840
cttctgccgc atcatgaggt aggcgataac tagcgttggg gagcggctat aaccttcccg    9900
gcagtggacg agcacccggc ctgtaagaaa caggggagac gtggtgagct gggggcgtcc    9960
catcacacca tggcgttggt caagactctt ccgtgaagtg ccacttaaaa gcacaatgtc   10020
acgccactgt gtgcctgcca gaatggctaa aatgaaaagg atggaaaacc caaagtgctg   10080
gtgaagatat ggggcaactg gaactcttct gcgtggctgg gggaggtgag gcgtgaattg   10140
gcacaaccac ttcggaaagc tgtgcggcac ggcggtatct cctcaagctg aacacgtgca   10200 tccctctgg cccagcaatc ccactcccag gcccaggtcc aatagagata cgcattcaca   10260
ttcacgaaca tgggccagaa tgttcacagg caacactgca catcatggcc cacagttaga   10320
aacccccaaa ggcccatcca cagtagaaag gacaaataca aagaatgacc agactgccac   10380
ttagcagaag caacacggag gcagcacaca catatgaggt ggatgagccc acagagtagg   10440
aaagcgggca aaaccatctg tgctgtcaga agcctgcaag gggctgggca cagtggctca   10500
cgcctgtaat cccagcactt tgggaggcca aggcaactgg atcacaaggt caggagttcg   10560
agaccagact ggccaacata gtgaaatccc gtctttacta aagatacaaa aaatagctg    10620 ggtgtggtgg cgcgagccta atcccagc tactcaggag gctgaggcca gagaattgct    10680
tgaacccagg aggcagaggt tgcggtgagg tgagattgtg ctgagattgt gctccagcct   10740
gggtgacaga gcgagactct gtctcaaaaa aaaaaagaag cccgcgtggc agaggccctg   10800
ggagctgggg atggggtgg tggagcatag agactggggg tgctttccag ggtgctggta    10860
gtgttttgtt tcttttttt tgagatggag tttccttctt gttgcccagg gtggagtgca    10920
gtggcgcgat ctcggctcac ttcagcctcc gcctcctggg ttcaagcaat tctcctgcct   10980
cagcctcctg agtagctggg actacaggcg catgccacca tgcccagcta attttttgt    11040 atcttttagt agagatgggg ttatttaat atagtgtgtg tgtgcgtgta tatatatg     11100 tgtatgtgtg tgtgtgtgtg tgtgtgtatg tgtgtgtata tatatatata taaatagaca   11160
ccatctctca atatccacag ggcagattgg ctccaggacc tcctgccgat acccaaatcc   11220
acagatgctc aagtccctga ttataaaatg acatcatata tgcaaataac ctctgcacag   11280
cacatcctcc cctatacttt aaatcatctc cagatgactt atgatacca agacaatgta    11340 aacatttatt agattatatc atctagagaa taatgacaag aaaaaaaatc tgtacatgtt   11400
cagtacagac ataacatctt tttatgttgt ttttaatatt tttcagactg cggttagttg   11460
aatccacaga tgtggaaccc acggatatgg aggaccgact gtatattcta ttggttctgt   11520 ttttttctaga gaatcctgac caatacactg gttattaact catgatccac ctaacctcaa   11580
ggtgcctcag ttttcttatc tggccaatag tacccattgc acaaggtggt tagaagatta   11640
aaggagagga cacatgaatc ctctaggtta gcacctggca tccatgtgca ctcaataaat   11700
gttacccaat actgggcatc ctctggtagc acctagtaca ccctcaacta cagcagccct   11760
```

```
ggtcctgtgt cattgccaga catgcgcaga ttgacttttc tctcccagag gacgaattct    11820
ttaagagcaa gaaatggccg gacacagtgg ctcacaccta taatcccaac actttgggag    11880
gtcgaggtgg gcggatcccc tgaagtcagg agttcgagac catcctggcc aacatggcga    11940
aaccccgttt ctactaaaaa tacaaaaaat tagctgggca tggtggcaca tgcctgtaat    12000
cccagctact cagaaagctg aggcaggaga atcacttgaa cctgggaggt ggagggtgca    12060
gtgagctgag attgagccac tgtactccag cctgggtgac aagagcgaga ctccgtctca    12120 aaaaaaaaa aaaaaggcaa gaaatgtggg gcattgattt ttggatgcgt tacaatctct    12180
agcatacact atgtgctcaa taaatatttg ctgactagct gagtgaatta ttacctacta    12240
acacctctat aaggccattg tttggcaagg aatctgctag cccagagtcc aacagagtct    12300
cttctgctcc tatcacccta cccccaaaac accactctat tttcccaatg ccttccaaat    12360
caggaagcag gagtcctcca cttttcttgcc cattcaccct ccggcctgta tgcccgaaat    12420
attcagagtg gggcttcccc tgccccaccc taggaatgag accctctgca gagcagccac    12480
cttaccatct agaacatact ctgcatgccc agtgcacaca gagcctactg ggaaaggggc    12540
cagttcaacc tcccattcct ctaggctcag cccagatgcc acctcctcca tgaagctgtt    12600
ttcccagcta gaagtgactg ctccctcttg agtaccctca gccatcccac ccagctctca    12660
gtgatgggtc cctgggcccc acacactgtt ggaggccagc atgtttctgt tgactcactt    12720
cgccactcat tcttagaagc atttatactt ggcattagag cccatggaat tcttcatcac    12780
ttgctcattc atcatttgca gtgtacctac tatgtgcctg atgctacatc aggtgctaag    12840
gagacagaca aggaacaaag tagacccagc ctgagggcag gcttcatgga agagaggaca    12900
tcatgccaag gacaaggtgg agtttgccag aggaaggggt agggagaggc agagagaact    12960
tttcagacta aagacccagc acacctggac tgagacaggt caaaaaaagg gcgtgttcct    13020
agttgtttgg aaagaggaaa caaagtcaga gagcttgaaa ttccctgaat gaataaccaa    13080
ttgctattat acgagaacaa caaaatcctt cccctccgcc cagcctatgt ttacacaggg    13140
tgaggaactc agtacagctg gagtggagga ggtgagcagg gttgggggt gacagtgacc    13200 aggaaggacc atgaggggcc tgtcagcaaa gtctgcagat actccgcagt aaagcttctc    13260
tctgagccct gagcgttcac tgtccagtgg tctagaaaat tctgtttact ggaaatcatt    13320
cagacagtga gcctgctggg cccaagagtc atcagtgtag tacagccaag gctgttcaca    13380
cctcatgggg gtcccctccg ctgggagggt ttggggtggg gagagaggaa gaggtaaagg    13440
gaggagctga gagaaacagc taaaagcaga aagggagaaa gggcaagtgg cccagcctgc    13500
tcagctgatg tctgctttgt ggccttctag ggtttcttgc tggaatgcct tggtgactgc    13560
cagcgccttg gtagttctcc ttcagtctta tcttatattt ggggggctgca ggaagtgttt    13620 cgtaagtggc tggaagattt ggccaggggg gctgtggttt gctgactgcc aacctaagct    13680
gaccgcagct accccttttc tccttgccag gcaatcacgt gaatctctag ccaatgagat    13740
gtgaggggta tttctgggaa atgttttact tgttcttaaa gagagagact gggcatggtg    13800
gcacgtgctt gtagtcccag ctactcagga ggctgaggtg agaggactgc ttgagcccag    13860
gagttggaga ccagtctaga caacatagca agaccctgtc tctttaaaaa agagagagag    13920
agtggccagg cgcggtggct catgcctgta atcccagcac tttgggaggc agaggaggc     13980 ggatcacctg aggtcaggag ttggagacca gcctgaccaa catggtgaaa ccccatctct    14040
actaaaaata caaaattagc caggcgtggg ggcgcatgcc tgtaatccca gctacttggg    14100
aggctgaggc gggaggctga ggcaggagaa tcgcttgaac ctgggaggtg gaggttgcgg    14160
```

```
tgagccaaga tcgcgccatt gctcttcagc ctgggcaaca agagtgaaac tccatctaaa    14220
aaaaaaaaaa aaaaggagag agagaagagg aaaaaaagag tgggaagaga tggctgcagg    14280
gcctcatctg ctgtactttg tcctgcttgg atgtggtgac tggatcccat cttgggacca    14340
tgacgggagc acccaacact gaggtggcag aagagagaaa gggaaagggc ctggtccaga    14400
ggccaccatg gagctgctga atcaagcagc cccttaatca accagacccc atgctccttc    14460
acctcaggac ttcttgccat gcacattaac acattaacac atcttcctca tcgttacagc    14520
tgtttgca                                                             14528
```